United States Patent [19]
Girard et al.

[11] Patent Number: 5,639,902
[45] Date of Patent: Jun. 17, 1997

[54] (CYCLOHEXYL)ALKENE COMPOUNDS

[75] Inventors: Jean-Pierre Girard, Montpellier; Pierre Hullot, Cournonterral; Claude Bonne, Montpellier; Jean-Claude Rossi, Montpellier; Roger Escale, Montpellier; Agnès Muller, Lattes, all of France

[73] Assignee: Adir et Compagnie, Courbevoie, France

[21] Appl. No.: 196,302

[22] Filed: Feb. 15, 1994

[30] Foreign Application Priority Data

Feb. 16, 1993 [FR] France .................... 93 01690

[51] Int. Cl.[6] .................................................. C07F 7/08
[52] U.S. Cl. ................... 556/437; 568/716; 568/731; 568/828; 562/508; 562/510; 560/126; 560/128
[58] Field of Search ................... 556/437; 568/716, 568/731, 828; 562/508, 510; 560/126, 128; 514/863, 63, 532, 416, 557, 625

[56] References Cited

U.S. PATENT DOCUMENTS 4,845,258  7/1989  Stahly ........................ 556/436

Primary Examiner—Paul F. Shaver
Attorney, Agent, or Firm—The Firm of Gordon W. Hueschen

[57] ABSTRACT

The invention relates to a compound selected from these of formula (I):

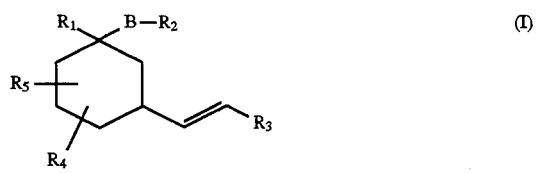

in which $R_1$, $R_2$, $R_3$, $R_4$, $R_5$ and B are as defined in the description, their enantiomers and diastereoisomers, their Z and E isomers, and their addition salts with a pharmaceutically-acceptable acid or base, and medicinal products containing the same which is useful for treating a disorder selected from an inflammatory disorder and a pathological inflammatory condition.

9 Claims, No Drawings

(CYCLOHEXYL)ALKENE COMPOUNDS

The present invention relates to new (cyclohexyl)alkene compounds, to processes for preparing them and to pharmaceutical compositions containing them.

Leukotriene $B_4$ ($LTB_4$) is a dihydroxylated icosatetraenoic acid arising from the metabolism of arachidonic acid. It is produced by many cells such as neutrophils, monocles and macrophages. $LTB_4$ is known to be an important participant in the activation of many functions of neutrophils. It stimulates the aggregation and degranulation of human neutrophils, induces leukocyte chimotaxis and is a promoter of the generation of superoxide radicals.

$LTB_4$ is consequently seen to be an important mediator of inflammation.

In man, $LTB_4$ has been detected, in particular, in rheumatoid synovial fluid, in the arthritic fluids of gout sufferers, in inflamed gastrointestinal mucosae and in the skin of individuals suffering from psoriasis (Critical Reviews in Immunology 1990, vol. 10 (1), p 1–12).

Neutrophils and many other cells possess specific membrane-bound $LTB_4$ receptors which mediate most of the responses of these cells to $LTB_4$.

Specific $LTB_4$ receptor antagonists would hence be useful to the clinician in the treatment of many inflammatory conditions or disorders in which $LTB_4$ participates as a pathological factor.

The Applicant has discovered new (cyclohexyl)alkene compounds which are potent $LTB_4$ receptor antagonists.

More especially, the invention relates to the compounds of formula (I):

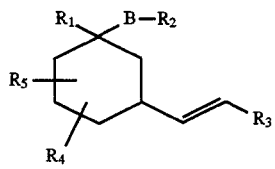

in which:

B represents an alkylene chain of 1 to 8 carbon atoms, unsubstituted or substituted with 1 or 2 alkyl radicals, $R_1$ represents a hydrogen atom or a radical chosen from hydroxyl and alkoxy, $R_2$ represents a radical chosen from: —$CH_2$—OH and

in which $R_6$ represents a group chosen from hydroxyl, alkoxy and

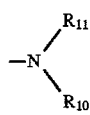

in which $R_{10}$ and $R_{11}$ each represent, independently of one another, a hydrogen atom, an alkyl radical or an aryl or arylalkyl group, the aryl or arylalkyl group being unsubstituted or substituted on the aryl with one or more radicals chosen from halogen, alkyl, alkoxy, and trifluoromethyl, or $R_{10}$ and $R_{11}$ alternatively form, together with the nitrogen atom which carries them, a heterocycle chosen from pyrrolidine, piperidine, piperazine, morpholine and thiomorpholine;

$R_3$ represents a group of formula:

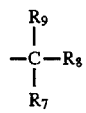

in which:

$R_7$ represents a radical chosen from hydroxyl, alkoxy and —O—$R_A$ in which $R_A$ represents an acyl or a group protecting the hydroxyl function, $R_9$ represents a hydrogen atom or a radical chosen from alkyl, aryl, and arylalkyl, the aryl or arylalkyl group being unsubstituted or substituted on the aryl with one or more radicals chosen form halogen, alkyl, alkoxy, and trifluoromethyl, or alternatively $R_7$ and $R_9$ form an oxo group, and $R_8$ represents a linear or branched alkyl group having 1 to 12 carbon atoms, unsubstituted or substituted with one or more radicals chosen from:

hydroxyl, halogen, unsubstituted aryl, aryl substituted with one or more radicals chosen from halogen, hydroxyl, alkyl, alkoxy and trifluoromethyl, unsubstituted cycloalkyl, cycloalkyl substituted with one or more radicals chosen from halogen, alkyl, oxo and alkoxy, it being possible for $R_8$ optionally to contain in its carbon skeleton:

one or two hetero atoms chosen from nitrogen, sulfur and oxygen, one or more unsaturated bonds, $R_4$ and $R_5$ represent, each independently of one another, a radical chosen from hydrogen and alkyl, or alternatively $R_4$ and $R_5$ form, together with the cyclohexane which carries them, a 1,2,3,4-tetrahydronaphthalene group or a perhydronaphthalene group, on the understanding that, in the description of the formula (I) and except where otherwise specified:

the terms "alkyl", "alkoxy" and "acyl" denote linear or branched groups containing 1 to 6 carbon atoms, the term "aryl" denotes a phenyl or naphthyl group, the term "unsaturated bond" denotes a double or triple bond, the term "cycloalkyl" denotes a group having 3 to 7 carbon atoms, their enantiomers and diastereoisomers, their Z and E isomers, and their addition salts with a pharmaceutically acceptable acid or base.

In particular, the alkyl radicals present in the different substituents of the formula (I) may be chosen from methyl, ethyl, n-propyl, isopropyl, n-butyl, isobutyl, sec-butyl, tert-butyl, pentyl or n-pentyl and hexyl or n-hexyl, as well as, in the case of $R_8$, also from heptyl, n-heptyl, octyl, n-octyl, nonyl, n-nonyl, decyl, n-decyl, undecyl, n-undecyl, dodecyl and n-dodecyl.

The alkoxy radicals present in the substituents of the formula (I) may be chosen from methoxy, ethoxy, n-propoxy, isopropoxy, n-butoxy, isobutoxy, sec-butoxy, tert-butoxy, pentyloxy and hexyloxy.

The halogens present in the substituents of the formula (I) may be chosen from bromine, chlorine, fluorine and iodine.

The cycloalkyls present in the substituents of the formula (I) may be chosen from cyclopropyl, cyclobutyl, cyclopentyl, cyclohexyl and cycloheptyl.

The O-protecting groups present, where appropriate, in the substituent $R_7$ are O-protecting groups known to a person skilled in the art, and preferably those which can be removed by mild acid hydrolysis, such as tert-butyldimethylsilyl, tetrahydro-2-pyranyl and methoxymethyl, methyldiphenylsilyl and tert-butyldiphenylsilyl groups.

The groups B present in the formula (I) may be chosen from methylene, ethylene, trimethylene, tetramethylene, pentamethylene, hexamethylene, heptamethylene and octamethylene.

Among pharmaceutically acceptable acids which may be used to form an addition salt with the compounds of the invention, there may be mentioned, by way of examples and without implied limitation, hydrochloric, sulfuric, phosphoric, tartaric, malic, maleic, fumaric, oxalic, methanesulfonic, ethanesulfonic, camphoric and citric acids.

Among pharmaceutically acceptable bases which may be used to salify the compounds used according to the invention, there may be mentioned, by way of examples and without implied limitation, sodium hydroxide, potassium hydroxide, triethylamine, diethylamine, ethanolamine, arginine, lysine and diethanolamine.

The invention also covers the process for preparing the compounds of formula (I), wherein:

a compound of formula (II):

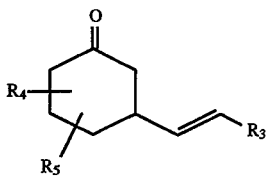

(II)

in which $R_3$, $R_4$ and $R_5$ are as described in the formula (I), is reacted with a compound of formula (III):

(III)

in which $R_2$ and B are as described in the formula (I), to obtain the corresponding compound of formula (I/a):

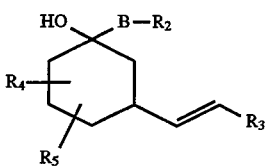

(I/a)

in which $R_2$, $R_3$, $R_4$, $R_5$ and B are as defined above, which may be, if so desired,
either subjected to the action of a compound of formula (IV):

(IV)

in which R' represents an alkyl, to obtain the compounds of formula (I/b):

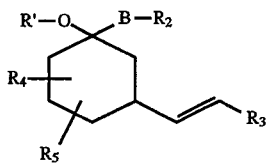

(I/b)

in which $R_2$, $R_3$, $R_4$, $R_5$, R' and B are as defined above, or subjected to tosyl chloride and then to a reduction with lithium aluminum hydride to yield the compound of formula (I/c):

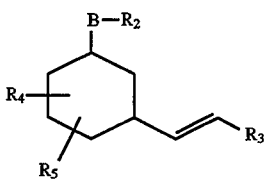

(I/c)

in which $R_2$, $R_3$, $R_4$, $R_5$ and B are as defined above, it being possible for the compounds of formula (I/a), (I/b), and (I/c) in which $R_9$ represents a hydrogen atom and $R_7$ represents a hydroxyl radical to be oxidized so as to obtain the compounds of formula (I/d):

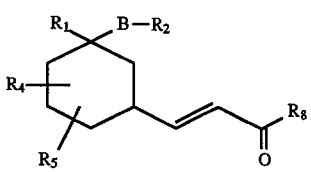

(I/d)

in which $R_1$, $R_2$, $R_4$, $R_5$, $R_8$ and B are as defined previously, the compounds of formula (I/a), (I/b), (I/c) and (I/d) representing the set of compounds of formula (I), which compounds of formula (I) are, if so desired, separated into their different enantiomers or diastereoisomers and salified, where appropriate, with a pharmaceutically acceptable acid or base.

The starting materials used in the process described above are either commercially available, or readily accessible to a person skilled in the art according to processes which are known in the literature or proposed in the preparation examples described below in this application.

The compounds of formula (II) are readily accessible to a person skilled in the art, by reaction of a compound of formula (II/a):

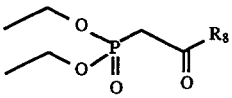

(II/a)

in which $R_8$ is as described in the formula (I) (obtained according to the method of SAVIGNAC P. et al, Tetrahedron Letters, 1976, pp 2829–2832), with a compound of formula (II/b):

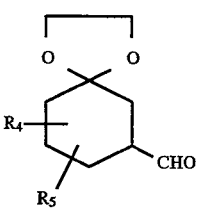

(II/b)

in which $R_4$ and $R_5$ are as defined in the formula (I), to obtain (according to the method of TAKACS J. M. et al.

Tetrahedron Letters, 1986, vol. 27, pp 1257–1260) a compound of formula (II/c):

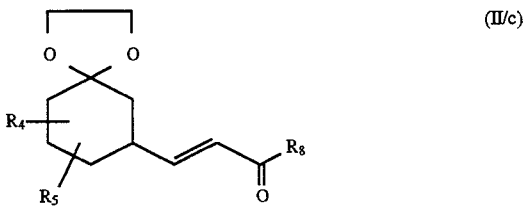

in which $R_4$, $R_5$, and $R_8$ are as defined above, which compound of formula (II/c) is either reduced, where appropriate selectively, to obtain a compound of formula (II/d):

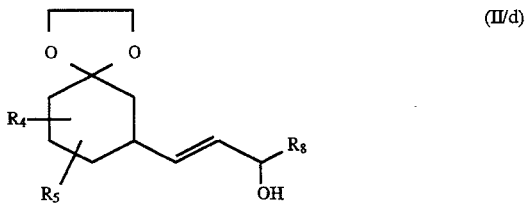

in which $R_4$, $R_5$ and $R_8$ are as defined above, which is then deprotected, after an alkylation, where appropriate, of the hydroxyl function, or submitted to the action of a nucleophilic $R_9$ with $R_9$ as defined in formula (I) to obtain, after the removing of the protection and an eventual alkylation of the hydroxyl function, the compound of formula (II/e):

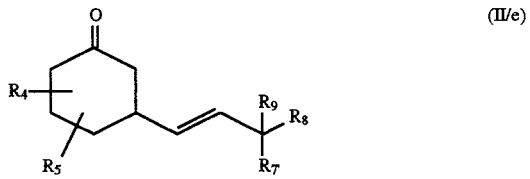

in which $R_4$, $R_5$, $R_8$ and $R_9$ are as defined above and $R_7$, represents a hydroxyl or alkoxy radical, in which compound of formula (II/e) the hydroxyl function represented, where appropriate, by $R_7$, may be acylated or protected by the grafting of an O-protecting group, to give a compound of formula (II/f):

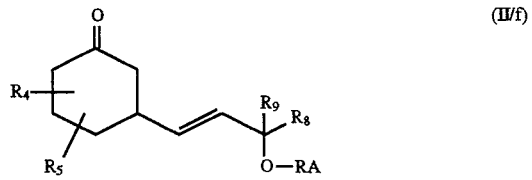

in which $R_4$, $R_5$, $R_8$ and $R_9$ are as defined above and $R_A$ is as defined in the formula (I), the compounds of formula (II/e) and (II/f) forming the set of compounds of formula (II).

The invention also covers the process for preparing the compounds of formula (I), wherein the separation of the diastereoisomers is carried out by column chromatography.

The invention also covers the process for preparing the compounds of formula (I), wherein the separation of the diastereoisomers is carried out by column chromatography and wherein the group $R_7$ of the compounds of formula (I) represents a tert-butyldimethylsilyloxy group.

The Applicant discovered that the compounds of the invention possessed noteworthy $LTB_4$ antagonist activity. They display, in particular, very high affinity for $LTB_4$ receptors.

This very considerable binding capacity is revealed in Example A of the present document (Study of binding of the compounds of the invention to $LTB_4$ receptors).

Strong antagonist activity of $LTB_4$ disclosed by the compounds of the invention is demonstrated in Examples B and C of the present document (Example B: Study of the activity of the compounds of the invention with respect to the chemotaxis of human PMN in vitro, and Example C: Study of the activity of the compounds of the invention with respect to the contraction of lung strips).

The compounds of the invention are hence seen to be potent antagonists of $LTB_4$ receptors and of the pathological mechanisms of which $LTB_4$ is the mediator.

By virtue of their action, the compounds of the invention are hence new candidates for the treatment and prevention of inflammatory disorders and of pathological inflammatory conditions.

The compounds of the invention are consequently useful in the treatment and prevention of chronic or acute joint, lung, skin or kidney inflammation, and in particular in the prevention and treatment of arthritis including rheumatoid arthritis, osteoarthrosis, psoriasis, allergic disorders, asthma, inflammatory disorders of the intestine, gastrointestinal ulcers, ischemia, atherosclerosis, respiratory distress and septic shock.

The subject of the present invention is also pharmaceutical compositions containing one of the compounds of formula (I), or one of its addition salts with a pharmaceutically acceptable acid or base, alone or in combination with one or more non-toxic, inert excipients.

Among the pharmaceutical compositions according to the invention, there may be mentioned, by way of examples and without implied limitation, those which are suitable for oral, parenteral, nasal, rectal, perlingual, ocular or pulmonary administration, and in particular injections, aerosols, eye or nasal drops, simple, film-coated or sugar-coated tablets, capsules including hard gelatin capsules, suppositories, creams, ointments and skin gels.

The appropriate dosage varies according to the patient's age and weight, the administration route and the nature of the complaint and of any associated treatments, and ranges between 0.1 mg and 100 mg per 24 hours taken in 1 to 2 doses.

The following preparations which are described are useful in the synthesis of the compounds of the invention. They do not form part of the invention.

TECHNICAL DATA

CHROMATOGRAPHY:

Thin-layer chromatography (TLC): silica gel 60 $F_{254}$ (Merck)

| | |
|---|---|
| Open-column chromatography: | Matrex silica, 60 Å, 70–200 mesh |
| | Matrex silica, 60 Å, 35–70 mesh |
| | (Amicon company) |

Gas chromatography (GC):

Delsi 30 apparatus

Split-splitless injector (split ratio: 1/20)

Hydrogen flame ionization detector

Fused silica capillary column (l=30 m, ∅=0.32 mm, 1 µDB5 film)

Carrier gas: helium, flow rate 2 cm³/min

Integrator-calculator: Enika 21

Ti: injection temperature program: oven temperature programming in °C./min tr: retention time in seconds.

MELTING POINT:

Melting points (m.p.) are taken in capillary tubes on a BUCHI TOTTOLI apparatus and are uncorrected.

INFRARED:

Infrared (IR) spectra are recorded on a BECKMANN ACCU-LAB-2 apparatus, in films on sodium chloride (NaCl) cells for liquids, or in potassium bromide (KBr) disks for solids.

NUCLEAR MAGNETIC RESONANCE (NMR)

Proton nuclear magnetic resonance spectra ($^1$H NMR) are recorded on a VARIAN EM 360 A apparatus at 60 MHz (reference: tetramethylsilane) and on a BRUKER WH 360 WB apparatus at 360 MHz.

$^1$H-$^1$H correlated spectra (COSY) are recorded on a BRUKER WH 360 WB apparatus at 360 MHz.

Phosphorus nuclear magentic resonance spectra ($^{31}$P NMR) are recorded decoupled on a BRUKER WP 2000 SY apparatus at 81.015 MHz (reference: phosphoric acid, external standard).

The values of the chemical shifts (δ) are given in pads per million (ppm), and those of the coupling constants (J) in hertz.

PREPARATION 1

3-[(E)-3-TERT-BUTYLDIMETHYLSILYLOXY-7-PHENYL-1-HEPTEN-1-YL]CYLOHEXANONE

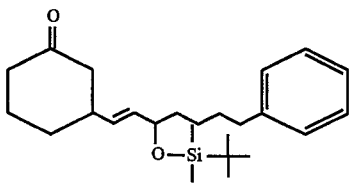

STAGE A

METHYL 3-HYDROXYCYCLOHEXANECARBOXYLATE

A solution of 100 g (658 mmol) of methyl 3-hydroxybenzoate in 280 cm$^3$ of ethanol is hydrogenated in the presence of 2.75 g of ruthenium on charcoal (5% Ru) under 100 bars pressure at 120° C. for 16 to 18 h.

After cooling, the solution is filtered through Celite and the catalyst is washed twice with 50 cm$^3$ of ether. The solvents are removed in a rotary evaporator, the residue is distilled under reduced pressure and 96.7 g (612 mmol) of methyl 3-hydroxycyclohexanecarboxylate are obtained.

Yield: 93%

B.p. (Boiling point) (1.33 Pa): 78° C.

Spectral characteristics:

IR (Infrared) (film, cm$^{-1}$): 3400 (νOH); 1720 (νC=O)

$^1$H NMR (CCl4) δ: 0.75 to 3 (m, 11H, OH and cyclohexyl H); 3.66 (s, 3H, OCH$_3$)

STAGE B

METHYL 3-OXOCYCLOHEXANECARBOXYLATE

A solution containing 36.9 g (369 mmol) of chromic anhydride, 74 cm$^3$ of distilled water and 21 cm$^3$ of concentrated sulfuric acid is added dropwise, in the course of 45 min and with stirring at between +5° and +10° C. to a solution of 58.3 g (369 mmol) of methyl 3-hydroxycyclohexanecarboxylate in 600 cm$^3$ of pure acetone. The medium, which immediately becomes red-brown, is stirred for 3 h at room temperature. 1 cm$^3$ of sulfuric acid and a few cm$^3$ of isopropanol are added to precipitate the chromium salts which are in solution, and a gradual decolorization of the medium is observed. The chromium salts are filtered off on Celite and washed with acetone. The filtrate is stirred for I h with sodium hydrogen carbonate and then concentrated in a rotary evaporator. The green residue is taken up with 500 cm$^3$ of ether and with 100 cm$^3$ of saturated sodium chloride solution. After settling has taken place, the aqueous layer is separated and extracted with ether. The combined organic phases are washed with saturated sodium chloride solution and then dried over sodium sulfate. After concentration, 47.2 g (302 mmol) of methyl 3-oxocyclohexanecarboxylate are obtained, which product is either used without further treatment or distilled under reduced pressure.

Yield: 82%

B.p. (5.32 Pa): 77°–80° C.

IR (film, cm$^{-1}$): 1720 (νC=O)

$^1$H NMR (CCl4) δ: 1.3 to 3 (m, 9H, cyclo H); 3.66 (s, 3H, OCH$_3$)

| Percentage analysis: C$_8$H$_{12}$O$_3$, M = 156.184 | | | | |
|---|---|---|---|---|
| Calc. %: | C | 61.52 | H | 7.74 |
| Measured: | | 61.78 | | 8.00 |

STAGE C

METHYL 3,3-(ETHYLENEDIOXY)CYCLOHEXANECARBOXYLATE

A solution composed of 30 g (192 mmol) of crude methyl 3-oxocyclohexanecarboxylate and 430 cm$^3$ of toluene is introduced into a one-liter three-necked flask equipped with a Dean and Stark apparatus, and 14.3 g (230 mmol) of ethylene glycol are then added with 814 mg (4.3 mmol) of para-toluenesulfonic acid monohydrate. The mixture is heated to reflux, the toluene-water azeotrope forms instantaneously and, after 40 min, no further refluxing of azeotrope (95° C.) takes place. The mixture is maintained for 6 h under reflux of the toluene (110° C.). After cooling, sodium hydrogen carbonate solution is added and the solution is then washed with saturated sodium chloride solution and dried over sodium sulfate. After concentration, 39 g of a yellow oil are obtained, which product is either distilled or chromatographed on a column of 215 g of silica (eluant: cyclo-hexane/ether, 98:2).

Note: chromatography is preferable to distillation, which partially deprotects the ketone.

Yield: 95%

B.p. (2660 Pa): 142° C.; b.p. (1.33 Pa): 64°–66° C.

IR (film, cm$^-$): 1700 (νC=O); 1040–1020 (νC—dioxolane)

$^1$H NMR CCl4) δ: 1 to 2.15 (m, 8H, cyclo CH$_2$); 2.2 to 2.9 (m, 1H, cyclo CH); 3.63 (s, 3H, OCH$_3$); 3.88 (s, 4H, O—CH$_2$—CH$_2$—O)

| Percentage analysis: C₁₀H₁₆O₄ M = 200.237 | | | | |
|---|---|---|---|---|
| Calc. %: | C | 59.98 | H | 8.05 |
| Measured: | | 60.16 | | 8.06 |

Reference: HOUSE, H. O. et al. J. Org. Chem, 1966, vol. 31 (8), pp 2667–9.

STAGE A'

DIETHYL METHYLPHOSPHONATE 188 g (1.32 mol) of methyl iodide are poured under nitrogen into a dry three-necked flask surmounted by an alcohol condenser (–10° C.), and then heated to the refluxing temperature. 168 g (1.02 mol) of triethyl phosphite are then added dropwise. The reaction is exothermic, and the temperature rises in the course of one hour to 73° C. The temperature of the mixture is maintained for one hour at between 70° and 75° C., and the solution is then cooled and concentrated in a rotary evaporator. The diethyl methylphosphonate is distilled under nitrogen, under reduced pressure.

Yield: 95%

B.p. (2660 Pa): =88°–90° C.

$^{31}$P NMR (81.015 MHz, CDCl₃) δ: +27.7

$^{1}$H NMR (360 MHz CDCl₃) δ: 1.35 (t, 6H, OCH₂—C$\underline{H}$₃, $^{3}$HH: 7Hz)1.40 (d, 3H, P(O)CH₃, $^{3}$PH=11 Hz); 4.02 (q, 4H, OC$\underline{H}$₂—CH₃, $^{3}$HH=7 Hz)

STAGE B'

5-PHENYLPENTANOYL CHLORIDE 51.44 g (289 mmol) of 5-phenylpentanoic acid and 44.65 g (375 mmol) of freshly distilled thionyl chloride are introduced under nitrogen into a 500 cm³ three-necked flask equipped with a condenser. The suspension is stirred and the medium is then brought gradually to 60° C. As soon as this temperature is reached, the medium is homogeneous; the temperature is maintained for 4 h. After a return to room temperature, the excess thionyl chloride is driven off in a rotary evaporator and the residue is distilled under reduced pressure.

54.5 g (277 mmol) of 5-phenylpentanoyl chloride, a colorless liquid, are obtained.

Yield: 96%

B.p. (1.33 Pa)=118°–120° C.

IR (film, cm$^{-1}$): 1790 (vC=O)

$^{1}$H NMR CCl4) δ: 1.5 to 2 (m, 4H, CH₂); 2.4 to 3.1 (m, 4H, CH₂C=O and CH₂Ph); 7.2 (s, 5H, aromatic H)

STAGE C'

DIETHYL (2-OXO-6-PHENYLHEXYL) PHOSPHONATE

Method: SAVIGNAC P. et al., Tetrahedron Letters, 1976, pp 2829–2832.

78 cm³ (110 mmol) of 1.41N n-butyllithium dissolved in hexane (the n-butyllithium is assayed immediately before use) are introduced under nitrogen into a dry 500-cm³ three-necked flask, and 80 cm³ of anhydrous tetrahydrofuran (THF) are added at –60° C. 15.2 g (100 mmol) of diethyl methylphosphonate in 20 cm³ of anhydrous THF are added dropwise (at –60° C.). The milky solution is stirred for 15 min at this temperature, and 20.93 g (110 mmol) of powdered copper iodide are then added in the course of 10 min. The brown suspension blackens progressively as the temperature rises, to –30° C. in the course of 30 min. Stirring is maintained at –30° C. for 1 h. The mixture is cooled again to –60° C., and 21.6 g (110 mmol) of 5-phenylpentanoyl chloride dissolved in 20 cm³ of anhydrous THF are added in the course of 15 min; the mixture remains black or decolorizes. The reaction mixture is stirred for 16 h while allowing the temperature to rise gradually. It is hydrolyzed with water, and the copper salts are filtered off on Celite and washed with dichloromethane. After settling has taken place, the aqueous layer is separated and extracted once with dichloromethane. The combined organic layers are washed with distilled water and then dried over sodium sulfate. After concentration in a rotary evaporator, 33.2 g of a yellow oil are obtained, which product is purified by chromatography on a column of 670 g of silica.

Elution is performed with pure ether, and then with ethyl acetate.

26.5 g (85 mmol) of pure diethyl (2-oxo-6-phenyl-hexyl) phosphonate are obtained.

Yield: 85%

IR (film, cm$^{-1}$): 1700 (vC=O); 1240 (vP=O); 1020–950 (vP—O)

$^{31}$P NMR (CDCl₃; 81.015 MHz) δ=+20.64

$^{1}$H NMR (360 MHz, CDCl₃) δ: 1.2 (t, 6H, CH₃, $^{J_{3}}_{HH}$=7 Hz); 1.52 (m, 4H, H₄, H₅); 2.5 (m, 4H, H₃, H₆); 2.92 (d, 2H, H₁, J$_{PH}$=22.47 Hz); 4.03 (m, 4H, H₁', $^{3}$J$_{PH}$=$^{3}$J$_{HH}$=7 Hz); 7.04 (m, 3H, aromatic H); 7.14 (m, 2H, aromatic H)

| Percentage analysis: C₁₆H₂₅O₄P M = 312.349 | | | | |
|---|---|---|---|---|
| Calc. %: | C | 61.52 | H | 8.06 |
| Measured: | | 61.33 | | 8.16 |

STAGE D

1,1-ETHYLENEDIOXY-3-[(E)-3-OXO-7-PHENYL-1-HEPTEN-1-YL]CYCLOHEXANE

Method: TAKACS J. M. et al., Tetrahedron Letters, 1986, vol. 27, pp 1257–1260.

A) Formation of the anion of the p-ketophosphonate obtained in Stage C'

36.4 g (116.7 mmol) of the p-ketophosphonate dissolved in 420 cm³ of anhydrous THF are introduced under nitrogen into a two-liter three-necked flask, and 5.6 g of sodium hydride in a 50% suspension in oil (116.7 mmol) are then added in several portions and with stirring. Reaction is immediate; a yellow coloration is observed. In parallel:

B) Reduction of the ester obtained in Stage C with DIBAL (diisobutylaluminum hydride=DIBAL)

21 g (105 mmol) of ester dissolved in 420 cm³ of anhydrous toluene are introduced under nitrogen into a one-liter three-necked flask and, after the solution has been cooled to –80° C., 105 cm³ (105 mmol) of a 1N solution of DIBAL in toluene are added dropwise in the course of 1 h. 30 min after completion of the addition, the reaction is monitored by gas chromatography.

Ti: 100C., program: 3° C./min

| tr (retention time) | aldehyde | 993 s | 89.4% |
|---|---|---|---|
| | alcohol | 1153 s | 3.2% |
| | ester | 1252 s | 4.8% |

The three-necked flask A is cooled to −35° C., and the aldehyde originating from the reduction of the ester (−78° C.) is then transferred to the anion in the course of 20 min using a cannula. The cold bath is removed, and the solution is brought back to room temperature in the course of 40 min and then stirred for 16 h. The medium is hydrolyzed with 100 cm³ of saturated sodium chloride solution and stirred for 1 h 30 min.

After filtration through Celite and washing with dichloromethane, the combined organic layers are washed with saturated sodium chloride solution and dried over sodium sulfate.

After concentration, 36.2 g of a yellow oil are obtained.

Since the ester obtained in Stage C above and the expected product have an identical migration coefficient (Rf), separation of these compounds is carried out by removal of the initial ester and the aldehyde by distillation (b.p. (1.33 Pa)=60°–70° C.) with a very short column. Gas chromatography after distillation reveals the value of this process (absence of ester and of intermediate aldehyde).

The residue is chromatographed on a column of 750 g of silica (cyclohexane/ether, 80:20) and yields 29.5 g (90 mmol) of 1,1-ethylenedioxy-3-[(E)-3-oxo-7-phenyl-1-hepten-1-yl]cyclohexane and 5.26 g (16.86 mmol) of initial β-ketophosphonate (16%).

Yield: 85.7%

IR (film, cm$^{-1}$): 1690 (vC=O); 1630 (vC=C);970 (vHC=CH trans)

$^1$H NMR CCl$_4$) δ: 0.8 to 2 (m, 12H, H$_{5'}$, H$_{6'}$, cyclo CH$_2$); 2.1 to 2.85 (m, 5H, H$_3$, H$_4$, H$_{7'}$); 3.87 (s, 4H, OCH$_2$–CH$_2$O); 5.94 (d, 1H, H$_{2'}$, J$_{H1'H2}$=17 Hz); 6.72 (dd, 1H, H$_{1'}$, J$_{H2}$=16Hz, J$_{H1'H3}$=6.1 Hz); 7.18 (m, 5H, aromatic H)

| Percentage analysis: C$_{21}$H$_{30}$O$_3$ M = 330.472 | | | |
|---|---|---|---|
| Calc. %: | C 76.33 | H | 9.15 |
| Measured: | 76.63 | | 9.32 |

STAGE E

1,1-ETHYLENEDIOXY-3-[(E)-3-HYDROXY-7-PHENYL-1-HEPTEN-1-YL]CYCLOHEXANE (according to GEMAL A. L. et al., J. Am. Chem. Soc., 1981, vol. 103, p 5454)

A solution of 40.05 g (122.1 mmol) of the compound obtained in Stage D in 400 cm³ of distilled methanol and 45.5g (122.12 mmol) of cerium chloride heptahydrate are introduced into a 1-liter three-necked flask. The temperature rises from 16 to 19° C., the mixture is stirred for 35 min and the salt gradually passes into solution. The flask is cooled to 9° C., and 4.65 g (123 mmol) of sodium borohydride are added in small portions in the course of 55 min (copious foaming). When the addition of the hydride is complete, the walls are rinsed with 70 cm³ of methanol, and the mixture is then left stirring for four hours while it returns gradually to room temperature. After cooling using a bath of ice-cold water, the mixture is hydrolyzed using 2N hydrochloric acid solution until the pH is neutral. 100 cm³ of saturated sodium chloride solution are then added. After settling has taken place, the aqueous phase is separated and extracted with ether, and the combined organic phases are washed with saturated sodium chloride solution and dried over sodium sulfate. After concentration, 40.12 g of 1,1-ethylenedioxy-3-[(E)-3-hydroxy -7-phenyl-1-hepten-1-yl) cyclohexane are obtained. The very slightly colored viscous oil obtained is used in the next step without purification.

Yield of crude product: 99.5%

IR (film, cm$^{-1}$): 3440 (vOH); 1660 (vC=C); 960 (μHC=CH trans)

$^1$H NMR (CCl4) δ: 0.75 to 1.9 (m, 12H, cyclo CH$_2$, H$_{5'}$, H$_{6'}$); 2 to 2.86 (m, 5H, H$_3$, H$_4$, H$_{7'}$); 3.87 (s, 4H, OCH$_2$–CH$_2$O); 3.85 to 4 (m, 1H, H$_{3'}$); 5.43 (m, 2H, H$_{1'}$, H$_{2'}$); 7.13 (m, 5H, aromatic H)

| Percentage analysis: C$_{21}$H$_{30}$O$_3$ M = 330.472 | | | |
|---|---|---|---|
| Calc. %: | C 76.33 | H | 9.15 |
| Measured: | 76.63 | | 9.32 |

STAGE E'

ENANTIOSELECTIVE REDUCTION OF THE KETONE OF STAGE D

According to E. J. COREY, R. K. BAKSHI, Tetrahedron Letters, 1990, 31, 611.

A solution composed of 2.055 g (6.22 mmol) of the ketone obtained in Stage D in 20 cm³ of anhydrous toluene (this solution is dried beforehand over 4 Å molecular sieve for 24 h) is introduced under nitrogen into a 100-cm³ three-necked flask. 0.185 g (0.627 mmol; 0.1 equivalent) of S-(−)-2-methyl-CBS-oxazaborolidine (Lancaster) is then added; the catalyst solubilizes in 20 min. The reaction medium is then cooled to −78° C., and a solution composed of 1.35 g (11.2 mmol; 2 equivalents) of catecholborane (Aldrich) diluted in 30 cm³ of anhydrous toluene is added in the course of 25 min. As soon as the first drops are added, the colorless reaction medium becomes yellow. After stirring at −78° C. for 21 h, the turbid milky solution is hydrolyzed with 35 cm³ of saturated sodium chloride solution, and 50 cm³ of dichloromethane are added. After a return to room temperature, stirring is maintained for 30 minutes, settling is then allowed to take place and the aqueous phase is separated and extracted 3 times with 50 cm³ of dichloromethane. The combined organic phases are washed 6 times with 10 cm³ of saturated sodium carbonate solution (the green aqueous layer is practically colorless at the third wash) and then twice with 20 cm³ of saturated sodium chloride solution and dried over sodium sulfate. After concentration, 2.415 g of a viscous red oil are obtained, which product is chromatographed on a column of 60 g of silica. The eluent cyclohexane/ether, 80:20 yields 250 mg of initial ketone (12%), and cyclohexane/ether, 75:25 yields 1.750 g (5.264 mmol) of the expected alcohol.

Yield of chromatographed product: 85%

The same procedure is used to obtain the S alcohol from R-(−)-2-methyl-CBS-oxazaborolidine (Lancaster).

STAGE F

3-[(E)-3-HYDROXY-7-PHENYL-1-HEPTEN-1-YL]CYCLOHEXANONE

According to HUET F. et al., Synthesis, 1978, 63.

50 cm³ of distilled dichloromethane and, with stirring, 30 g of silica and 1.5 g of 15% sulfuric acid solution are introduced into a 250-cm³ round-bottomed flask. After cooling using a bath of ice-cold water, a solution composed of 8.22 g (24.9 mmol) of the crude compound obtained in Stage E in 35 cm³ of dichloromethane is added. After stirring for 16 hours at room temperature, 1.5 g of sodium hydrogen carbonate are added and the mixture is stirred for 3 hours. After filtration through sintered glass, the silica is washed with dichloromethane, and the filtrate is washed with saturated sodium chloride solution and then dried over sodium sulfate. After concentration, 6.42 g of a thick yellow liquid are obtained, which product is chromatographed on a column of 150 g of silica.

5.508 g (19.25 mmol) of pure 3-[(E)-3-hydroxy-7-phenyl-1-hepten-1-yl] cyclohexanone are isolated (eluent: cyclohexane/ether, 65:35).

Yield: 77.5%

IR (film, cm⁻¹): 3320 (νOH); 1690 (νC=O)

¹H NMR (CCl₄) δ: 0.8 to 2.8 (m, 17H, cyclo H, H₄' to H₇'); 3.93 (m, 2H, H₃', and hydroxyl); 5.46 (m, 2H, H₁', H₂'); 7.1 (5H, aromatic H)

| Percentage analysis: C₁₉H₂₆O₂ M = 286.418 | | | | |
|---|---|---|---|---|
| Calc. %: | C | 79.67 | H | 9.14 |
| Measured: | | 79.43 | | 9.15 |

STAGE G

3-[(E)-3-TERT-BUTYLDIMETHYLSILYLOXY-7-PHENYL-1-HEPTEN-1-YL]CYCLOHEXANONE

A solution composed of 23.37 g of 1,8-diazabicyclo[5.4.0]undec-7-ene (153.5 mmol) in 160 cm³ of anhydrous dichloromethane and 19.3 g (128 mmol) of tert-butyldimethylsilyl chloride are introduced under nitrogen into a 500-cm³ three-necked flask. After cooling to 0° C., a solution of 30.5 g (106.64 mmol) of the compound obtained in the preceding stage in 100 cm³ of anhydrous dichloromethane is added dropwise. The medium is stirred for 48 h at room temperature and then hydrolyzed with 50 cm³ of distilled water. The aqueous phase is extracted with ether. The organic phases are washed with 1N hydrochloric acid solution, then with sodium hydrogen carbonate solution and with distilled water; after they have been dried over sodium sulfate and concentrated, 44.45 g of the expected product are obtained, which product is purified by chromatography on a column of 1130 g of silica.

40.1 g (100.2 mmol) of pure 3-[(E)-3-tert-butyl-dimethylsilyloxy-7-phenyl-1-hepten-1-yl]cyclohexanone are isolated (eluent:cyclohexane/ether, 97:3).

Yield: 94%

IR (film, cm⁻¹): 1710 (νC=O); 1250 (νSi—OH₃); 1065–1090 (νSiO—C); 840–870 (νSi—OH₃)

¹H NMR (CCl₄ without TMS): 0.0 (s, 6H, dimethylsilyl); 0.9 (s, 9H, tert-butylsilyl); 0.8 to 2.8 (17H, cyclo H, H₄'to H₇'); 3.9 (1H, H₃'); 5.46 (m, 2H, H₁', H₂'); 7.1 (5H, aromatic H)

| Percentage analysis: C₂₅H₄₀O₂Si M = 400.679 | | | | |
|---|---|---|---|---|
| Calc. %: | C | 74.94 | H | 10.06 |
| Measured: | | 75.09 | | 10.27 |

PREPARATION 2

3-[(E)-3-TERT-BUTYLDIMETHYLSILYLOXY-1-UNDECEN-1-YL]CYCLOHEXANONE

Employing the procedure described in Preparation 1, but replacing 5-phenylpentanoyl chloride in Stage C' by nonanoyl chloride, the compound of the title is obtained. IR (film, cm⁻¹): 1705 (νC=O); 1245 (νSi—CH₃); 960 (νHC=OH trans); 825 (νSi—O—C)

PREPARATION 3

3-[(E)-3-TERT-BUTYLDIMETHYLSILYLOXY-1-OCTEN-1-YL]CYCLOHEXANONE

According to Corey E. J. et al., J. Am. Chem. Soc. 1972, vol. 94, pp 7210–7211.

PREPARATIONS 4 TO 12

Employing the procedure described in Preparation 1, but using the appropriate acyl halide in Stage C', the following are obtained successively:

PREPARATION 4

3-[(E)-3-TERT-BUTYLDIMETHYLSILYLOXY-6-PHENOXY-1-HEXEN-1-YL]CYCLOHEXANONE

PREPARATION 5

3-[(E)-3-TERT-BUTYLDIMETHYLSILYLOXY-13-PHENOXY-1-TRIDECEN-1-YL]CYCLOHEXANONE

PREPARATION 6

3-[(E)-3-TERT-BUTYLDIMETHYLSILYLOXY-4-(4-CHLOROPHENYL)-1-BUTEN-1-YL]CYCLOHEXANONE

PREPARATION 7

3-[(E)-3-TERT-BUTYLDIMETHYLSILYLOXY-6-(3,4-DIMETHOXYPHENYL)-1-HEXEN-1-YL]CYCLOHEXANONE

PREPARATION 8

3-[(E)-3-TERT-BUTYLDIMETHYLSILYLOXY-4,4-DIMETHYL-1-PENTEN-1-YL]CYCLOHEXANONE

PREPARATION 9

3-[(E)-3-TERT-BUTYLDIMETHYLSILYLOXY-4-(4-TRIFLUOROMETHYL-PHENYL)-1-BUTEN-1-YL]CYCLOHEXANONE

PREPARATION 10

3-[(E)-3-TERT-BUTYLDIMETHYLSILYLOXY-1-DECEN-1-YL]CYCLOHEXANONE

PREPARATION 11

3-[(E)-3-TERT-BUTYLDIMETHYLSILYLOXY-5-CYCLOPENTYL-1-PENTEN-1-YL]CYCLOHEXANONE

PREPARATION 12

3-[(E)-3-TERT-BUTYLDIMETHYLSILYLOXY-7-PHENYL-1-HEPTEN-1-YL]TETRALONE

Employing the procedure described in Preparation 1, but replacing methyl 3-oxocyclohexanecarboxylate obtained in Stage B by methyl 1-tetralone-3-carboxylate obtained after esterification of 1-tetralone-3-carboxylic acid (Biochem. Biophys. Acta, 1987; vol. 916 (2); pp 205–212), the compound of Preparation 12 is obtained.

EXAMPLE 1

ETHYL 1-HYDROXY-3-[(E)-3-TERT-BUTYLDIMETHYLSILYLOXY-7-PHENYL-1-HEPTEN-1-YL]-1-CYCLOHEXANEACETATE

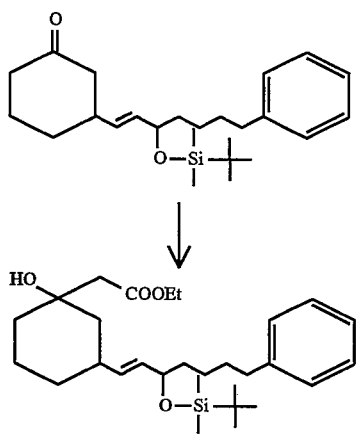

In a 1-liter three-necked flask under nitrogen, 39.8 cm$^3$ (99.5 mmol) of a solution of n-butyllithium (2.5N in hexane) are added dropwise in the course of thirty minutes at −80° C. to a solution composed of 12.05 g (119 mmol) of diisopropylamine (freshly distilled) in 400 cm$^3$ of anhydrous THF. After 40 min of stirring at −78° C., 9.9 g (112.5 mmol) of ethyl acetate (freshly distilled) dissolved in 70 cm$^3$ of anhydrous THF are added dropwise in the course of 30 min. The medium is stirred for 30 min at −78° C., and 24.84 g (62.1 mmol) of the compound obtained in Preparation 1 dissolved in 140 cm$^3$ of anhydrous THF are then added dropwise. After stirring for 16 h while allowing the temperature to rise, the mixture is hydrolyzed with 70 cm$^3$ of ice-cold water.

The aqueous phase is extracted with ether, and the combined organic phases are washed twice with 50 cm$^3$ of distilled water and dried over sodium sulfate.

EXAMPLES 2 AND 3

DIASTEREOISOMERS OF ETHYL 1-HYDROXY-3-[(E)-3-TERT-BUTYLDIMETHYLSILYLOXY-7-PHENYL-1-HEPTEN-1-YL]-1-CYCLOHEXANE-ACETATE

EXAMPLE 2

ETHYL (1S*,3S*)-1-HYDROXY-3-[(E)-3-TERT-BUTYLDIMETHYLSILYLOXY-7-PHENYL-1-HEPTEN-1-YL]-1-CYCLOHEXANEACETATE

EXAMPLE 3

ETHYL (1R*,3S*)-1-HYDROXY-3-[(E)-3-TERT-BUTYLDIMETHYLSILYLOXY-7-PHENYL-1-HEPTEN-1-YL]-1-CYCLOHEXANEACETATE 32.95 g of the compound obtained in Example 1 are chromatographed on a column of 1200 g of silica to obtain a first separation of two isomers (Example 2 and Example 3) (eluent: cyclohexane/ether, 92:8).

Note: Proton NMR (CCl$_4$ without TMS) enables the two isomers to be differentiated (even at 60 MHz), especially in respect of the $\underline{CH_2}$COOEt protons; those of Example 2 have a chemical shift of 2.33 and those of Example 3 of 2.50. This has the advantage that the separation of the two isomers can be monitored by NMR.

At this point in the synthesis, it is essential to have access to extremely pure products; for this reason, the compounds of Examples 2 and 3 isolated during the chromatography are further subjected to high performance liquid chromatography or HPLC (R SIL SiO$_2$ 10 µ column, L 250, Ø 22, eluent: cyclohexane/ether (85:15), flow rate 8 cm$^3$/min, UV 260 nm detector, injection: 150 to 200 mg).

After HPLC chromatography, the following are isolated:

EXAMPLE 2

ETHYL (1S*,3S*)-1-HYDROXY-3-[(E)-3-TERT-BUTYLDIMETHYLSILYLOXY-7-PHENYL-1-HEPTEN-1-YL]-1-CYCLOHEXANEACETATE the less polar isomer 12.9 g (26.4 mmol)

Yield: 42.5%

$^1$H NMR (CDCl$_3$ without TMS) δ: 0.00 (d, 6H, dimethylsilyloxy); 0.86 (m, 9H, tert-butyl-silyloxy); 1.03 (m, 2H, H$_{2'}$); 1.26; 1.19 to 1.9 (m, 15H, ester methyl, H$_{4'}$ to H$_{6'}$, H$_{4''}$ to H$_{6''}$); 2.15 to 2.7 (m, 3H, H$_{3'}$ and H$_{7''}$), 2.33 (s, 2H, H$_2$); 3.2 (m, 1H, hydroxyl); 3.96 (m, 1H, H$_{3''}$), 4.2 (q, 2H, ester methylene, J=7 Hz); 5.4 (m, 2H, H$_{1''}$, H$_{2''}$); 7.1 (m, 5H, aromatic H)

EXAMPLE 3

ETHYL (1R*,3S*)-1-HYDROXY-3-[(E)-3-TERT-BUTYLDIMETHYLSILYLOXY-7-PHENYL-1-HEPTEN-1-YL]-1-CYCLOHEXANEACETATE the more polar isomer 15 g (30.73 mmol)

Yield: 49.5%

$^1$H NMR (CDCl$_3$ without TMS) δ: 0.00 (d, 6H, dimethylsilyloxy); 0.9 (m, 9H, tert-butylsilyloxy); 1.03 (m, 2H, H$_{2'}$); 1.26; 1.2 to 1.9 (m, 15H, ester methyl, H$_{4'}$ to H$_{6'}$, H$_{4''}$ to H$_{6''}$); 2.15 to 2.6 (m, 3H, H$_{3'}$ and H$_{7''}$); 2.50 (s, 2H, H$_2$) ;3.5 (m, 1H, hydroxyl); 3.95 (m, 1H, H$_{3''}$); 4.18 (q, 2H, ester methylene, J=7 Hz); 5.4 (m, 2H, H$_{1''}$, H$_{2''}$); 7.1 (m, 5H, aromatic H)

Physical characteristics common to the compounds of Examples 2 and 3: IR (film, cm$^{-1}$) (Examples 2 and 3) 3500 (νOH); 1710 (νC=O); 1250 (νSiCH$_3$); 1065–1090 (νSi—O—C); 830 and 770 (νSi—CH$_3$)

| Percentage analysis: C$_{29}$H$_{48}$O$_4$Si M = 488.78 | | | | |
|---|---|---|---|---|
| Calc. %: | C | 71.33 | H | 9.9 |
| Measured: | | 71.46 | | 10.16 |

EXAMPLE 4

ETHYL (1S*,3S*)-1-HYDROXY-3-[(E)-3-HYDROXY-7-PHENYL-1-HEPTEN-1-YL]-1-CYCLOHEXANEACETATE 14.3 g (29.3 mmol) of compound of Example 2 dissolved in 310 cm$^3$ of distilled THF are introduced into a 1-liter round-bottomed flask and, after the solution has been cooled to 0° C., 42 cm³ (42 mmol) of 1N hydrochloric acid are added. After a return to room temperature, the medium is stirred for 64 h, and 6.9 g (84 mmol) of sodium hydrogen carbonate are then added. The medium is concentrated in a rotary evaporator and then taken up with 500 cm³ of ether. The aqueous phase is extracted with ether, and the combined organic phases are washed twice with 50 cm³ of distilled water and dried over sodium sulfate. After concentration, 10.95 g of an oil corresponding to the compound of the title are obtained.

EXAMPLES 5 AND 6

DIASTEREOISOMERS OF ETHYL (1S*,3S*)-1-HYDROXY-3-[(E)-3-HYDROXY-7-PHENYL-1-HEPTEN-1-YL]-1-CYCLOHEXANEACETATE

EXAMPLE 5

ETHYL (1S*,3S*)-1-HYDROXY-3-[(3S*R*,E)-3-HYDROXY-7-PHENYL-1-HEPTEN-1-YL]-1-CYCLOHEXANEACETATE

EXAMPLE 6

ETHYL (1S*,3S*)-1-HYDROXY-3-[(3R*S*,E)-3-HYDROXY-7-PHENYL-1-HEPTEN-1-YL]-1-CYCLOHEXANEACETATE

The compound obtained in Example 4 is chromatographed on a column of 600 g of silica in order to separate the two isomers.

The eluent cyclohexane/ether, 60:40 yields 3.62 g of a mixture (compound of Example 5/compound of Example 6) which contains chiefly the compound of Example 5 (10:90), then 3.190 g of a second mixture (approximately 50:50), then 3.6 g of a mixture (approximately 15:85), equivalent to 10.41 g (27.83 mmol) in all.

Yield (deprotection+chromatography):95%

The last two fractions of the mixtures are further subjected separately to high performance liquid chromatography (HPLC): eluent: cyclohexane/ethyl acetate, 85:15, and yield 1.964 g of the pure compound of Example 5 and 3.50 g of the pure compound of Example 6 (9.37 mmol).

Yield, compound of Example 6: 32%

IR (film, cm⁻¹): 3410 (vOH); 1720 (vC=O); 1185 (vC—O—C); 960 (vHC=CH trans)

¹H NMR (360 MHz, CDCl₃) δ: - compound of Example 5: (the less polar isomer): Ethyl (1S*,3S*)-1-hydroxy-3-[(3S*R*,E)-3-hydroxy-7-phenyl-1-hepten-1-yl)-1-cyclohexaneacetate 0.97 (m, 2H, H₂'); 1.22; 1.13 to 1.75 (m, 15H, ester methyl; H₄' to H₆', H₄" to H₆"); 2.37 (s, 2H, H₂); 2.43 (m, 1H, H₃'); 2.55 (m, 2H, H₇"); 3.95 (q, 1H, H₃"', $J_{H3"H4"}=J_{H3"H2"}=6.4$ Hz); 4.10 (q, 2H, ester methylene, J=7.2 Hz); 5.35 (dd, 1H, H₂"', $J_{H1"H2"}=15.5$ Hz, $J_{H2"H3"}=6.1$ Hz); 5.46 (dd, 1H, H₁"', $J_{H1"H2"}=15.5$ Hz, $J_{H1"H3}=6.1$ Hz); 7.15 (m, 5H, aromatic H)

Compound of Example 6: (the more polar isomer): Ethyl (1S*,3S*)-1-hydroxy-3-[(3R*S*,E)-3-hydroxy-7-phenyl-1-hepten-1-yl)-1-cyclohexaneacetate

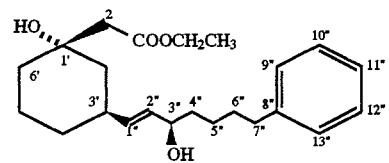

(Example 6)

Spectral characteristics: ¹H NMR (360 MHz, CDCl₃) δ: 1.0 (m, 2H, H₂'); 1.26; 1.14 to 1.83 (m, 15H, ester methyl, H₄' to H₆', H₄" to H₆"); 2.41 (s, 2H, H₂); 2.43 (m, 1H, H₃'); (t, 2H, H₇"); 4 (q, 1H, H₃"', $J_{H3"H4"}=J_{H3"H2"}=6.4$ Hz); 4.16 (q, 2H, ester methylene, J=7.2 Hz); 5.40 (dd, 1H, H₂"', $J_{H1"H2"}=15.5$ Hz, $J_{H2"H3"}=6.1$ Hz); 5.51 (dd, 1H, H₁"', $J_{H1"H2"}=15.5$ Hz, $J_{H1"H3"}=6.1$ Hz); 7.15 (m, 5H, aromatic H)

¹³C NMR (CDCl₃, 90 MHz) DEPT 135 and COSY (H, C). 172.8 (C₁); 142.6 (C₈"); 136.9 (C₁"); 131 (C₂"); 130.8 (C₁₀"—C₁₂"); 128.4 (C₉"—C₁₃"); 125.6 (C₁₁"); 73.1 (C₃"); 69.8 (C₁'); 60.6 (ester methylene C); 46.9 (C₂); 43.1 (C₂'); 37.2 (C₆'); 37 (C₅'); 36.6 (C₇"); 35.9 (C₃'); 32 (C₄'); 31.4 (C₆"); 25.1 (C₄"); 20.9 (C₅"); 14.2 (ester methyl C)

UV on the compound of Example 6 (cyclohexane) λ max: 262 nm

ε: 224

Mass spectrography (EI, 20 eV):
Compound of Example 5
m/z: 338 (M—H₂O)
Compound of Example 6
FAB⁺: m Na⁺ Calc. 397.2354796
Measured 397.3367000 Δ: 3.1 ppm

| Percentage analysis: compound of Example 5: $C_{23}H_{34}O_4$ M = 374.52 | | | | | | |
|---|---|---|---|---|---|---|
| Calc. % | C | 73.76 | H | 9.15 | O | 17.09 |
| Measured |  | 73.50 |  | 9.22 |  | 17.46 |
| compound of Example 6 | | | | | | |
| Measured |  | 73.50 |  | 9.21 |  | 17.55 |

EXAMPLE 7

(1S*,3S*)-1-HYDROXY-3-[(3R*S*,E)-3-HYDROXY-7-PHENYL-1-HEPTEN-1-YL]-1-CYCLOHEXANE-ACETIC ACID 387 mg (1.035 mmol) of the compound of Example 6 dissolved in 20 cm³ of methanol are introduced into a 100-cm³ round-bottomed flask, and 1.55 cm³ of 1N sodium hydroxide (1.55 mmol) and 20 cm³ of water are added to the cooled solution. The mixture is stirred for 24 hours and then concentrated in a rotary evaporator. The crude product is taken up with 50 cm³ of water and 50 cm³ of ether. The aqueous phase is acidified with 1N hydrochloric acid solution and then extracted 3 times with 50 cm³ of ether. The ether layer is dried over sodium sulfate and then concentrated. The crude product is recrystallized (ether/cyclohexane): white crystals. Melting point=87° C.

IR (film, cm⁻¹): 3640 and 2600 (vOH); 1730 (vC=O); 960 (vHC=CH trans)

NMR (250 MHz, CDCl₃) δ: 1.0 (m, 2H, H₂'); 1.26; 1.15 to 1.9 (m, 12H, H₄' to H₆', H₄" to H₆"); 2.47 (s, 2H, H₂); 2.43 (m, 1H, H₃'); 2.6 (t, 2H, H₇", J=7.4 Hz); 4.04 (q, 1H, H₃"', $J_{H3"H4"}, J_{H3"H2"}=6.4$ Hz); 4.4 (m, 3H, hydroxyls); 5.42 (dd, 1H, H₂"', $J_{H1"H2"}=15.5$ Hz, $J_{H2"H3"}=6.1$ Hz); 5.53 (dd, 1H, H₁"', $J_{H1"H2"}=15.5$ Hz, $J_{H1"H3"}=6.1$ Hz); 7.15 (m, 5H, aromatic H)

| Percentage analysis: $C_{21}H_{30}O_4$ M = 346.47 | | | | | | |
|---|---|---|---|---|---|---|
| Calc. %: | C | 72.80 | H | 8.73 | O | 18.47 |
| Measured | | 72.70 | | 8.78 | | 18.17 |

Sodium (1S*,3S*)-1-hydroxy-3-[(3R*S*,E)-3-hydroxy-7-phenyl-1-hepten-1-yl]-1-cyclohexaneacetate:

501 mg (1.44 mmol) of (1S*,3S*)-1-hydroxy-3-[(3R*S*,E)-3-hydroxy-7-phenyl-1-hepten-1-yl]-1-cyclohexaneacetic acid are introduced into a 250-cm³ round-bottomed flask and dissolved in 20 cm³ of methanol. After 10 cm³ of distilled water have been added, the acid is neutralized with 0.04N sodium hydroxide solution, monitoring the reaction with a pH meter (pH 8.3). The opalescent solution is concentrated in a rotary evaporator to remove the alcohol and then washed twice with 10 cm³ of distilled ether. The solution is concentrated again in a rotary evaporator to remove the traces of ether and then lyophilized overnight. The white solid (526 mg), which is tacky, is taken up with 50 cm³ of distilled water, and the light yellow solution is filtered through a 0.45 m Millipore filter with a prefilter. The lyophilized clear solution yields 509 mg of white salt which is subjected to vacuum exhaustion (6.65 Pa) for 10 h at room temperature.

$C_{21}H_{29}O_4Na$ M: 368

Solubility of the salt in water: 100 g/L

Clear, slightly yellow solution

Stability of the solution: more than 18 months

EXAMPLE 8

ETHYL (1R*,3S*)-1-HYDROXY-3-[(E)-3-HYDROXY-7-PHENYL-1-HEPTEN-1-YL]-1-CYCLOHEXANEACETATE

By replacing, in Example 4, the compound obtained in Example 2 by the compound of Example 3, the product of the title is obtained.

EXAMPLES 9 AND 10

DIASTEREOISOMERS OF ETHYL (1R*,3S*)-1-HYDROXY-3-[(E)-3-HYDROXY-7-PHENYL-1-HEPTEN-1-YL]-1-CYCLOHEXANEACETATE

Employing the procedure described in Examples 5 and 6, but separating by chromatography the isomers of ethyl (1R*,3S*)-1-hydroxy-3-[(E)-3-hydroxy-7-phenyl-1-hepten-1-yl]-1-cyclohexaneacetate, the following are obtained:

EXAMPLE 9

ETHYL (1R*,3S*)-1-HYDROXY-3-[(3S*R*,E)-3-HYDROXY-7-PHENYL-1-HEPTEN-1-YL]-1-CYCLOHEXANEACETATE

EXAMPLE 10

ETHYL (1R*,3S*)-1-HYDROXY-3-[(3R*S*,E)-3-HYDROXY-7-PHENYL-1-HEPTEN-1-YL]-1-CYCLOHEXANEACETATE

Yield (for both diastereoisomers): 76%

IR (film, cm$^{-1}$): 3410 (vOH); 1720 (vC=O); 1180 (vC—O—C); 960 (vHC=CH trans)

NMR (360 MHz, CDCl$_3$) δ:

compound of Example 9, the less polar:

ETHYL (1R*,3S*)-1-HYDROXY-3-[(3S*R*,E)-3-HYDROXY-7-PHENYL-1-HEPTEN-1-YL]-1-CYCLOHEXANEACETATE 0.97 (m, 2H, H$_{2'}$); 1.22; 1.13 to 1.9 (m, 15H ester methyl, H$_{4'}$ to H$_{6'}$, H$_{4''}$ to H$_{6''}$); 2 (m, 1H, H$_{3'}$); 2.52 (s, 2H, H$_2$); 2.53 (t, 2H, H$_{7''}$, J=7.4 Hz); 3.95 (q, 1H, H$_{3''}$, J$_{H3''H4''}$=J$_{H3''H2''}$=6.4 Hz); 4.09 (m, 2H, ester methylene); 5.37 (dd, 1H, H$_{2''}$, J$_{H1''H2''}$=15.5 Hz, J$_{H2''H3''}$=6.1 Hz); 5.5 (dd, 1H, H$_{1''}$, J$_{H1''H2''}$=15.5 Hz, J$_{H1''H3''}$=6.1 Hz); 7.15 (m, 5H, aromatic H)

compound of Example 10, the more polar:

ETHYL (1R*,3S*)-1-HYDROXY-3-[(3R*S*,E)-3-HYDROXY-7-PHENYL-1-HEPTEN-1-YL]-1-CYCLOHEXANEACETATE 0.97 (m, 2H, H$_{2'}$); 1.22; 1.13 to 1.8 (m, 15H, ester methyl, H$_{4'}$ to H$_{6'}$, H$_{4''}$ to H$_{6''}$); 2 (m, 1H, H$_{3'}$); 2.5 (s, 2H, H$_2$); 2.53 (t, 2H, H$_{7''}$, J=7.4 Hz); 3.96 (q, 1H, H$_{3''}$, J$_{H3''H4''}$=J$_{H3''H2''}$=6.4 Hz); 4.12 (m, 2H, ester methylene); 5.37 (dd, 1H, H$_{2''}$, J$_{H1''H2''}$=15.5 Hz, J$_{H2''H3''}$=6.1 Hz); 5.5 (dd, 1H, H$_{1''}$, J$_{H1''H2''}$=15.5 Hz, J$_{H1''H3''}$=6.1 Hz); 7.15 (m, 5H, aromatic H)

MS (EI, 20 eV): compounds of Examples 9 and 10 m/z: 356 (374-H$_2$O)

EXAMPLE 11

ETHYL 1-HYDROXY-3-[(E)-3-TERT-BUTYLDIMETHYLSILYLOXY-1-UNDECEN-1-YL]-1-CYCLOHEXANEACETATE

Employing the procedure described in Example 1, but replacing the compound of Preparation 1 by the compound of Preparation 2, the compound of the title is obtained.

EXAMPLES 12 AND 13

DIASTEREOISOMERS OF ETHYL 1-HYDROXY-3-[(E)-3-TERT-BUTYLDIMETHYLSILYLOXY-1-UNDECEN-1-YL]-1-CYCLOHEXANEACETATE

Employing the procedure described in Examples 2 and 3, but separating by chromatography on silica the isomers of the compound of Example 11, the following are obtained:

EXAMPLE 12

ETHYL (1S*,3S*)-1-HYDROXY-3-[(E)-3-TERT-BUTYLDIMETHYLSILYLOXY-1-UNDECEN-1-YL]-1-CYCLOHEXANEACETATE

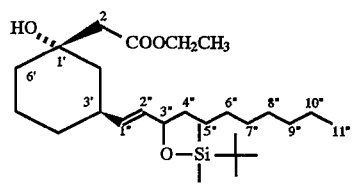

(Example 12)

EXAMPLE 13

ETHYL (1R*,3S*)-1-HYDROXY-3-[(E)-3-TERT-BUTYLDIMETHYLSILYLOXY-1-UNDECEN-1-YL]-1-CYCLOHEXANEACETATE

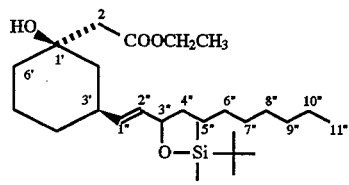

(Example 13)

Overall yield (both isomers): 86.5%

Chromatographic system used:

HPLC, Nucleosil 10 μ, eluent: cyclohexane/ether, 90:10

IR (film, cm$^{-1}$): (compounds 12 and 13): 3460 (vOH); 1710 (vC=O); 1245 (vSi—CH$_3$); 960 (vHC=OH trans); 825-765 (vSi—CH$_3$)

$^1$H NMR (CDCl$_3$, 360 MHz) δ:

compound of Example 12 (the less polar)

0.0 (d, 6H, dimethylsilyl); 0.84 (m, 12H, tert-butylsilyl, H$_{11''}$); 1.03 (m, 2H, H$_{2'}$); 1.26; 1.22 and 1.11 to 1.8 (m, 25H, ester methyl, H$_{4'}$ to H$_{6'}$, H$_{4''}$ to H$_{10''}$); 2.4 (s, 2H, H$_2$); 2.41 (m, 1H, H$_{3'}$); 3.37 (m, 1H, hydroxyl); 3.96 (q, 1H, H$_{3''}$, J$_{H3''H4''}$=J$_{H3''H2''}$=6.4 Hz); 4.16 (q, 2H, ester methylene, J=7.2 Hz); 5.31 (dd, 1H, H$_{2''}$, J$_{H1''H2''}$=15.5 Hz, J$_{H2''H3''}$=6.1 Hz); 5.38 (dd, 1H, H$_{1''}$, J$_{H1''H2''}$=15.5 Hz, J$_{H1''H3}$=6.1 Hz)

compound of Example 13 (the more polar)

0.0, (d, 6H, dimethylsilyl); 0.85 (m, 12H, tert-butylsilyl, H$_{11''}$); 1.02 (m, 2H, H$_{2'}$); 1.26; 1.22 and 1.1 to 1.8 (m, 25H, ester methyl, H$_{4'}$ to H$_{6'}$, H$_{4''}$ to H$_{10''}$); 2.02 (m, 1H, H$_{3'}$); 2.57 (m, 2H, H$_2$); 3.83 (m, 1H, hydroxyl); 3.97 (q, 1H, H$_{3''}$, J$_{H3''H4''}$=J$_{H3''H2''}$=6.4 Hz); 4.17 (q, 2H, ester methylene, J=7.2 Hz); 5.32 (dd, 1H, H$_{2''}$, J$_{H1''H2''}$=15.5 Hz, J$_{H2''H3''}$=6.1 Hz); 5.40 (dd, 1H, H$_{1''}$, J$_{H1''H2''}$=15.5 Hz, J$_{H1''H3}$=6.1 Hz)

EXAMPLE 14

ETHYL (1S*,3S*)-1-HYDROXY-3-[(E)-3-HYDROXY-1-UNDECEN-1-YL]-1-CYCLOHEXANEACETATE

Employing the procedure used for Example 4, but replacing the compound of Example 2 by the compound of Example 12, the product of the title is obtained.

EXAMPLES 15 AND 16

Employing the procedure described in Examples 5 and 6, but separating the diastereoisomers of Example 14, the following are obtained:

EXAMPLE 15

ETHYL (1S*,3S*)-1-HYDROXY-3-[(3S*R*,E)-3-HYDROXY-1-UNDECEN-1-YL]-1-CYCLOHEXANEACETATE

EXAMPLE 16

ETHYL (1S*,3S*)-1-HYDROXY-3-[(3R*S*,E)-3-HYDROXY-1-UNDECEN-1-YL]-1-CYCLOHEXANEACETATE

Eluent: cyclohexane/ethyl acetate (85:15)

IR (film, cm$^{-1}$): compounds 15 and 16:3400 (vOH); 1710 (vC=O); 1200 (vC—O—C)

$^1$H NMR (CDCl$_3$, 360 MHz) δ:

compound of Example 15 (the less polar)

0.85 (m, 3H, H$_{11''}$); 1.05 (m, 2H, H$_2$,0; 1.25; 1.24 and 1.16 to 1.83 (m, 25H, ester methyl, H$_{4'}$ to H$_{6'}$, H$_{4''}$ to H$_{10''}$); 2.40 (s, 2H, H$_2$); 2.42 (m, 1H, H$_{3'}$); 3.99 (q, 1H, J$_{H3''H4''}$=J$_{H3''H2''}$=6.4 Hz); 4.15 (q, 2H, ester methylene, J=7.2 Hz); 5.42 (dd, 1H, H$_{2''}$, J$_{H1''H2''}$=15.5 Hz, J$_{H2''H3''}$=6.1 Hz); 5.52 (dd, 1H, H$_{1''}$, J$_{H1''H2''}$=15.5 Hz, J$_{H1''H3}$=6.1 Hz)

compound of Example 16 (the more polar)

0.85 (t, 3H, H$_{11''}$); 1.05 (m, 2H, H$_{2'}$); 1.25; 1.24 and 1.16 to 1.83 (m, 25H, ester methyl, H$_{4'}$ to H$_{6'}$, H$_{4''}$ to H$_{10''}$); 2.40 (s, 2H, H$_2$); 2.42 (m, 1H, H$_{3'}$); 4 (q, 1H, H$_{3''}$, J$_{H3''H4''}$=J$_{H3''H2''}$=6.4 Hz); 4.15 (q, 2H, ester methylene, J=7.2 Hz); 5.42 (dd, 1H, H$_{2''}$, J$_{H1''H2''}$=15.5 Hz, J$_{H2''H3''}$=6.1 Hz); 5.52 (dd, 1H, H$_{1''}$, J$_{H1''H2''}$=15.5 Hz, J$_{H1''H3}$=6.1 Hz)

Compounds of Examples 15 and 16—mass spectrography (EI, 20 eV): m/z: 318 (354-2H$_2$O)

EXAMPLE 17

ETHYL (1R*,3S*)-1-HYDROXY-3-[(E)-3-HYDROXY-1-UNDECEN-1-YL]-1-CYCLOHEXANEACETATE

Employing the procedure used for Example 4, but replacing the compound of Example 2 by the compound of Example 13, the product of the title is obtained.

EXAMPLES 18 AND 19

Employing the procedure used for Examples 5 and 6, but separating the diastereoisomers of Example 17, the following are obtained:

EXAMPLE 18

ETHYL (1R*,3S*)-1-HYDROXY-3-[(3S*R*,E)-3-HYDROXY-1-UNDECEN-1-YL]-1-CYCLOHEXANEACETATE

EXAMPLE 19

ETHYL (1R*,3S*)-1-HYDROXY-3-[(3R*S*,E)-3-HYDROXY-1-UNDECEN-1-YL]-1-CYCLOHEXANEACETATE

Eluent: cyclohexane/ethyl acetate, 80:20

Compound of Example 18 (the less polar): yield: 37%

Compound of Example 19 (the more polar): yield: 42.5%

IR (film, cm$^{-1}$): compounds 18 and 19: 3400 (vOH); 1720 (vC=O); 1200 (vC—O—C)

EXAMPLES 20 TO 25

Employing the procedure described in Examples 1 to 6, but starting in Example 1 from the compound of Preparation 3 and permitting the grafting of methyl butyrate instead of ethyl acetate at position I of the cyclohexanone, the following are obtained successively:

EXAMPLE 20

METHYL 1-HYDROXY-3-[(E)-3-TERT-BUTYLDIMETHYLSILYLOXY-1-OCTEN-1-YL]-1-CYCLOHEXANEBUTYRATE

EXAMPLE 21

METHYL (1S*,3S*)-1-HYDROXY-3-[(E)-3-TERT-BUTYLDIMETHYLSILYLOXY-1-OCTEN-1-YL]-1-CYCLOHEXANEBUTYRATE

EXAMPLE 22

METHYL (1R*,3S*)-1-HYDROXY-3-[(E)-3-TERT-BUTYLDIMETHYL-SILYLOXY-1-OCTEN-1-YL]-1-CYCLOHEXANEBUTYRATE

EXAMPLE 23

METHYL (1S*,3S*)-1-HYDROXY-3-[(E)-3-HYDROXY-1-OCTEN-1-YL]-1-CYCLOHEXANEBUTYRATE

EXAMPLE 24

METHYL (1S*,3S*)-1-HYDROXY-3-[(3S*R*,E)-3-HYDROXY-1-OCTEN-1-YL]-1-CYCLOHEXANEBUTYRATE

EXAMPLE 25

METHYL (1S*,3S*)-1-HYDROXY-3-[(3R*S*,E)-3-HYDROXY-1-OCTEN-1-YL]-1-CYCLOHEXANEBUTYRATE

EXAMPLES 26 TO 28

Employing the procedure described in Examples 4 to 6, but starting from the compound obtained in Example 22, the following are obtained:

EXAMPLE 26

METHYL (1R*,3S*)-1-HYDROXY-3-[(E)-3-HYDROXY-1-OCTEN-1-YL]-1-CYCLOHEXANEBUTYRATE

EXAMPLE 27

METHYL (1R*,3S*)-1-HYDROXY-3-[(3S*R*,E)-3-HYDROXY-1-OCTEN-1-YL]-1-CYCLOHEXANEBUTYRATE

EXAMPLE 28

METHYL (1R*,3S*)-1-HYDROXY-3-[(3R*S*,E)-3-HYDROXY-1-OCTEN-1-YL]-1-CYCLOHEXANEBUTYRATE

EXAMPLES 29 TO 32

By subjecting the compounds obtained in Examples 24, 25, 27 and 28 to treatment with potassium hydroxide, the following are obtained successively:

EXAMPLE 29

POTASSIUM (1S*,3S*)-1-HYDROXY-3-[(3S*R*,E)-3-HYDROXY-1-OCTEN-1-YL]-1-CYCLOHEXANEBUTYRATE

EXAMPLE 30

POTASSIUM (1S*,3S*)-1-HYDROXY-3-[(3R*S*,E)-3-HYDROXY-1-OCTEN-1-YL]-1-CYCLOHEXANEBUTYRATE

EXAMPLE 31

POTASSIUM (1R*,3S*)-1-HYDROXY-3-[(3S*R*,E)-3-HYDROXY-1-OCTEN-1-YL]-1-CYCLOHEXANEBUTYRATE

EXAMPLE 32

POTASSIUM (1R*,3S*)-1-HYDROXY-3-[(3R*S*,E)-3-HYDROXY-1-OCTEN-1-YL]-1-CYCLOHEXANEBUTYRATE

EXAMPLES 33 TO 38

Employing the procedure described in Examples 1 to 6, but using in Example 1 the compound obtained in Preparation 3 instead of the compound of Preparation 1, the following are obtained successively:

EXAMPLE 33

ETHYL 1-HYDROXY-3-[(E)-3-TERT-BUTYLDIMETHYLSILYLOXY-1-OCTEN-1-YL]-1-CYCLOHEXANEACETATE

EXAMPLE 34

ETHYL (1S*,3S*)-1-HYDROXY-3-[(E)-3-TERT-BUTYLDIMETHYLSILYLOXY-1-OCTEN-1-YL]-1-CYCLOHEXANEACETATE

EXAMPLE 35

ETHYL (1R*,3S*)-1-HYDROXY-3-[(E)-3-TERT-BUTYLDIMETHYLSILYLOXY-1-OCTEN-1-YL]-1-CYCLOHEXANEACETATE

EXAMPLE 36

ETHYL (1S*,3S*)-1-HYDROXY-3-[(E)-3-HYDROXY-1-OCTEN-1-YL]-1-CYCLOHEXANEACETATE

EXAMPLE 37

ETHYL (1S*,3S*)-1-HYDROXY-3-[(3S*R*,E)-3-HYDROXY-1-OCTEN-1-YL]-1-CYCLOHEXANEACETATE

EXAMPLE 38

ETHYL (1S*,3S*)-1-HYDROXY-3-[(3R*S*,E)-3-HYDROXY-1-OCTEN-1-YL]-1-CYCLOHEXANEACETATE

EXAMPLES 39 TO 41

Employing the procedure described in Examples 4 to 6, but starting from the compound obtained in Example 35, the following are obtained successively:

EXAMPLE 39

ETHYL (1R*,3S*)-1-HYDROXY-3-[(E)-3-HYDROXY-1-OCTEN-1-YL]-1-CYCLOHEXANEACETATE

EXAMPLE 40

ETHYL (1R*,3S*)-1-HYDROXY-3-[(3S*R*,E)-3-HYDROXY-1-OCTEN-1-YL]-1-CYCLOHEXANEACETATE

EXAMPLE 41

ETHYL (1R*,3S*)-1-HYDROXY-3-[(3R*S*,E)-3-HYDROXY-1-OCTEN-1-YL]-1-CYCLOHEXANEACETATE

EXAMPLES 42 TO 45

Employing the procedure described in Example 7, but replacing the compound of Example 6 by the compounds of Examples 37, 38, 40 and 41, the following are obtained successively:

EXAMPLE 42

(1S*,3S*)-1-HYDROXY-3-[(3S*R*,E)-3-HYDROXY-1-OCTEN-1-YL]-1-CYCLOHEXANEACETIC ACID

EXAMPLE 43

(1S*,3S*)-1-HYDROXY-3-[(3R*S*)-3-HYDROXY-1-OCTEN-1-YL]-1-CYCLOHEXANEACETIC ACID

EXAMPLE 44

(1R*,3S*)-1-HYDROXY-3-[(3S*R*)-3-HYDROXY-1-OCTEN-1-YL]-1-CYCLOHEXANEACETIC ACID

EXAMPLE 45

(1R*,3S*)-1-HYDROXY-3-[(3R*S*)-3-HYDROXY-1-OCTEN-1-YL]-1-CYCLOHEXANEACETIC ACID

EXAMPLES 46 TO 54

Employing the procedure described in Example 1, but starting from the compounds obtained in Preparations 4 to 12, the following are obtained successively:

EXAMPLE 46

ETHYL 1-HYDROXY-3-[(E)-3-TERT-BUTYLDIMETHYLSILYLOXY-6-PHENOXY-1-HEXEN-1-YL]-1-CYCLOHEXANEACETATE

EXAMPLE 47

ETHYL 1-HYDROXY-3-[(E)-3-TERT-BUTYLDIMETHYLSILYLOXY-13-PHENOXY-1-TRIDECEN-1-YL]-1-CYCLOHEXANEACETATE

EXAMPLE 48

ETHYL 1-HYDROXY-3-[(E)-3-TERT-BUTYLDIMETHYLSILYLOXY-4-(4-CHLOROPHENYL)-1-BUTEN-1-YL]-1-CYCLOHEXANEACETATE

EXAMPLE 49

ETHYL 1-HYDROXY-3-[(E)-3-TERT-BUTYLDIMETHYLSILYLOXY-6-(3,4-DIMETHOXYPHENYL)-1-HEXEN-1-YL]-1-CYCLOHEXANEACETATE

EXAMPLE 50

ETHYL 1-HYDROXY-3-[(E)-3-TERT-BUTYLDIMETHYLSILYLOXY-4,4-DIMETHYL-1-PENTEN-1-YL]-1-CYCLOHEXANEACETATE

EXAMPLE 51

ETHYL 1-HYDROXY-3-[(E)-3-TERT-BUTYLDIMETHYLSILYLOXY-4-(4-TRIFLUOROMETHYLPHENYL)-1-BUTEN-1-YL]-1-CYCLOHEXANEACETATE

EXAMPLE 52

ETHYL 1-HYDROXY-3-[(E)-3-TERT-BUTYLDIMETHYLSILYLOXY-1-DECEN-1-YL]-1-CYCLOHEXANEACETATE

EXAMPLE 53

ETHYL 1-HYDROXY-3-[(E)-3-TERT-BUTYLDIMETHYLSILYLOXY-5-CYCLOPENTYL-1-PENTEN-1-YL]-1-CYCLOHEXANEACETATE

EXAMPLE 54

ETHYL 1-HYDROXY-3-[(E)-3-TERT-BUTYLDIMETHYLSILYLOXY-7-PHENYL-1-HEPTEN-1-YL]-1,2,3,4-TETRAHYDRONAPHTHALENE-1-ACETATE

EXAMPLES 55 TO 63

Employing the procedure described in Example 4, but replacing the compound of Example 2 by the compounds of Examples 46 to 54, the following are obtained successively:

EXAMPLE 55

ETHYL 1-HYDROXY-3-[(E)-3-HYDROXY-6-PHENOXY-1-HEXEN-1-YL]-1-CYCLOHEXANEACETATE

EXAMPLE 56

ETHYL 1-HYDROXY-3-[(E)-3-HYDROXY-13-PHENOXY-1-TRIDECEN-1-YL]-1-CYCLOHEXANEACETATE

EXAMPLE 57

ETHYL 1-HYDROXY-3-[(E)-3-HYDROXY-4-(4-CHLOROPHENYL)-1-BUTEN-1-YL]-1-CYCLOHEXANEACETATE

EXAMPLE 58

ETHYL 1-HYDROXY-3-[(E)-3-HYDROXY-6-(3,4-DIMETHOXYPHENYL)-1-HEXEN-1-Y L]-1-CYCLOHEXANEACETATE

EXAMPLE 59

ETHYL 1-HYDROXY-3-[(E)-3-HYDROXY-4,4-DIMETHYL-1-PENTEN-1-YL]-1-CYCLOHEXANEACETATE

EXAMPLE 60

ETHYL 1-HYDROXY-3-[(E)-3-HYDROXY-4-(4-TRIFLUOROMETHYLPHENYL)-1-BUTEN-1-YL]-1-CYCLOHEXANEACETATE

EXAMPLE 61

ETHYL 1-HYDROXY-3-[(E)-3-HYDROXY-1-DECEN-1-YL]-1-CYCLOHEXANEACETATE

EXAMPLE 62

ETHYL 1-HYDROXY-3-[(E)-3-HYDROXY-5-CYCLOPENTYL-1-PENTEN-1-YL]-1-CYCLOHEXANEACETATE

EXAMPLE 63

ETHYL 1-HYDROXY-3-[(E)-3-HYDROXY-7-PHENYL-1-HEPTEN-1-YL]-1,2,3,4-TETRAHYDRONAPHTHALENE-1-ACETATE

EXAMPLES 64 AND 65

Employing the procedure used in Examples 54 and 63, but replacing 1,2,3,4-tetrahydronaphthalene by perhydronaphthalene, the following are obtained successively:

EXAMPLE 64

ETHYL 1-HYDROXY-3-[(E)-TERT-BUTYLDIMETHYLSILYLOXY-7-PHENYL-1-HEPTEN-1-YL]-PERHYDRONAPHTHALENE-1-ACETATE

EXAMPLE 65

ETHYL 1-HYDROXY-3-[(E)-3-HYDROXY-7-PHENYL-1-HEPTEN-1-YL]-PERHYDRONAPHTHALENE-1-ACETATE

EXAMPLES 66 AND 67

EXAMPLE 66

(1S*,3S*)-1-HYDROXY-3-[(E)-3-TERT-BUTYLDIMETHYLSILYLOXY-7-PHENYL-1-HEPTEN-1-YL]-CYCLOHEXANE-1-(N,N-DIMETHYLACETAMIDE)

EXAMPLE 67

(1R*,3S*)-1-HYDROXY-3-[(E)-3-TERT-BUTYLDIMETHYLSILYLOXY-7-PHENYL-1-HEPTEN-1-YL]-CYCLOHEXANE-1-(N,N-DIMETHYLACETAMIDE)

according to T. CUVIGNY, P. HULLOT, M. LARCHEVEQUE and H. NORMANT, Compte rendus, 279, series C, 1974, 569.

3.8 cm$^3$ (5.19 mmol) of a solution of n-butyl-lithium (1.36N in hexane) are added dropwise in the course of ten min at −80° C. to a solution composed of 0.631 g (6.24 mmol) of diisopropylamine (freshly distilled) in 20 cm$^3$ of anhydrous THF. After forty minutes of stirring at −78° C., 0.511 g (5.87 mmol) of N,N-dimethylacetamide (freshly distilled) dissolved in 3 cm³ of anhydrous THF is added dropwise in the course of thirty minutes at −60° C. The medium is stirred for thirty minutes at −60° C., and 1.3 g (3.24 mmol) of ketone obtained in Preparation 1 dissolved in 3 cm³ of anhydrous THF are then added dropwise. After stirring for 16 h while allowing the temperature to rise, the mixture is hydrolyzed with 20 cm³ of ice-cold water.

The aqueous phase is extracted with dichloromethane, and the combined organic phases are washed twice with 20 cm³ of saturated sodium chloride solution and dried over sodium sulfate.

After concentration, 1.7 g of crude product are obtained, which product is chromatographed on a column of 50 g of silica to obtain a first separation of the two isomers of Examples 66 and 67 (eluent: cyclohexane/ether (50:50)).
NOTE:

Proton NMR (CCl₄ without TMS) enables the two isomers to be differentiated (even at 100 MHz), especially in respect of the CH₂CONMe₂ protons; those of the compound of Example 66 have a chemical shift of 2.33, and those of the compound of Example 67 of 2.49. This has the advantage that the separation of the two isomers can be monitored by NMR.

At this point in the synthesis, it is essential to have access to extremely pure products; for this reason, the compounds of Examples 66 and 67 isolated during the chromatography (cyclohexane/ether, 40:60) are further subjected to HPLC. R SIL SiO₂ 10 p. column, L 250, µ22 eluent: dichloromethane/methanol (99.1:0.9), flow rate 12 cm³/min UV 260 nm detector After HPLC chromatography, the following are isolated:

(1S*,3S*)-1-hydroxy-3-[(E)-3-tert-butyldimethylsilyloxy-7-phenyl-1-hepten-1-yl]-cyclohexane-1-(N,N-dimethylacetamide) (0.715 g (1.467 mmol)—yield: 45.8%), (1R*,3S*)-1-hydroxy-3-[(E)-3-tert-butyldimethylsilyloxy-7-phenyl-1-hepten-1-yl]-cyclohexane-1-(N,N-dimethylacetamide) (0.401 g (0.8228 mmol)—yield: 25.9%)

Overall yield: 71.1%

IR (film, cm⁻¹): compounds of Examples 66 and 67: 3400 (νOH); 1620 (νC=O); 1250 (νSi—CH₃); 1065–1090 (νSi—O—C); 830 and 770 (νSi—CH₃);

¹H NMR (CDCl₃ without TMS, 360 MHz) δ:
compound of Example 66: (the less polar isomer)

0.01 (m, 6H, dimethylsilyloxy); 0.85 (m, 9H, tert-butylsilyloxy); 0.93 (m, 2H, H₂·); 1 to 1.87 (m, 12H, H₄·, to H₆·, H₄·· to H₆··); 2.35 (s, 2H, H₂); 2.45 (m, 1H, H₃); 2.55 (m, 2H, H₇··); 2.94 (s, 3H, N-CH₃); 3.02 (s, 3H, N-CH₃); 3.96 (m, 1H, H₃··); 5.1 (d, 1H, hydroxyl); 5.36 (m, 2H, H₁··, H₂··); 7.2 (m, 5H, aromatic H)

compound of Example 67: (the more polar isomer)

0.01 (m, 6H, dimethylsilyloxy); 0.85 (m, 9H, tert-butylsilyloxy); 1.01 (m, 1H, H₄'ₐ); 1.27 (m, H₂'ₐ); 1.29 (m, H₅··, and H₅'ₐ); 1.37 (m, H₆'ₐ); 1.43 (m, H₄··); 1.58 (t, 2H, ³J=7.5, H₆··); 1.65 (m, H₄'ᵦ); 1.70 (m, H₅'ᵦ); 1.84 (m, 2H, H₆'ᵦ and H₂'ᵦ) 1.96 (m, 1H, H₃); 2.51 (m, 2H, H₂); 2.57 (t, 2H, ³J: 7.2, H₇··); 2.94 (s, 3H, N-CH₃); 3.02 (s, 3H, N-CH₃); 3.97 (m, 1H, H₃); 5.32 (dd, 1H, $J_{H2''H1''}$=6.1, $J_{H2''H1''}$15.4; H₂··); 5.40 (dd, 1H, $J_{H1''H2''}$=15.4, $J_{H1''H3''}$=6.1, H₁··); 5.69 (d, 1H, ³J=5.0, OH); 7.14 (m, 3H, H₉··, H₁₁··, H₁₃··); 7.24 (t, 2H, ³J=7.5, H₁₀··, H₁₂··) ¹H/¹H correlation (CDCl₃): (H₉··; H₁₀··); (H₉··, H₇··); (OH; H₂); (H₁··, H₃·) (H₂··, H₃··); H₃··; H₄··); (H₇··; H₆··); (H₃·; H₂'ᵦ); (H₃·; H₂'ₐ); (H₃·; H₄'ₐ); (H₃·; H₄'ᵦ); (H₆'ᵦ; H₆'ₐ); (H₆'ᵦ; H₅'ᵦ); (H₆'ᵦ; H₅'ₐ); (H₅'ᵦ; H₅'ₐ); (H₅'ᵦ; H₄'ₐ); (H₅'ᵦ; H₄'ᵦ); (H₄'ₐ; H₄'ᵦ); (H₂'ₐ; H₂'ᵦ); (CH₃-t-Bu; Si-CH₃)

| Percentage analysis: C₂₉H₄₉NO₃Si M = 487.348 | | | | | | |
|---|---|---|---|---|---|---|
| Calc. % | C | 71.41 | H | 10.13 | N | 2.87 |
| Measured | | 71.48 | | 9.90 | | 3.02 |

EXAMPLES 68 AND 69

EXAMPLE 68

(1S*,3S*)-1-HYDROXY-3-[(3S*R*,E)-3-HYDROXY-7-PHENYL-1-HEPTEN-1-YL]CYCLOHEXANE-1-(N,N-DIMETHYLACETAMIDE)

EXAMPLE 69

(1S*,3S*)-1-HYDROXY-3-[(3R*S*,E)-3-HYDROXY-7-PHENYL-1-HEPTEN-1-YL]CYCLOHEXANE-1-(N,N-DIMETHYLACETAMIDE)

0.626 g (1.28 mmol) of compound of Example 66 dissolved in 14 cm³ of distilled THF is introduced into a 25-cm³ round-bottomed flask and, after the solution has been cooled to 0° C., 1.93 cm³ (1.93 mmol) of 1N hydrochloric acid are added. After a return to room temperature, the medium is stirred for 64 h, and 0.336 g (4 mmol) of sodium hydrogen carbonate is then added. The medium is concentrated in a rotary evaporator and then taken up with 50 cm³ of ether. The aqueous phase is extracted with ether, and the combined organic phases are washed twice with 5 cm³ of distilled water and dried over sodium sulfate. After concentration, 0.650 g of an oil is obtained, which product is chromatographed on a column of 37 g of silica in order to isolate the two isomers corresponding to Examples 68 and 69.

Elution with ethyl acetate yields 0.430 g of a mixture of the two isomers (1.154 mmol).

Yield (deprotection+chromatography): 90%

The isomers are purified (or separated) by HPLC with ethyl acetate as eluent, and yield 0.405 g of the pure compounds of Examples 68 and 69 (1.087 mmol).

Yield (deprotection+chromatography+HPLC): 85%

IR (film, cm⁻¹): 3410 (νOH); 1620 (νC=O); 1185 (νC—O—C); 960 (νHC=CH trans)

¹H NMR (CDCl₃, 360 MHz)

compound of Example 68: (the less polar isomer)

(1S*,3S*)-1-hydroxy-3-[(3S*R*,E)-3-hydroxy-7-phenyl-1-hepten-1-yl]cyclohexane-1-(N,N-dimethylacetamide) 0.97 (m, 2H, H₂·); 1.13 to 1.75 (m, 12H, H₄·, to H₆·, H₄··, to H₆··); 2.37 (s, 2H, H₂); 2.46 (m, 1H, H₃); 2.55 (t, 2H, H₇··); 2.94 (s, 3H, N-CH₃); 3.02 (s, 3H, N-CH₃); 3.95 (q, 1H, H₃··, $J_{H3''H4''}$=$J_{H3''H2''}$=6.4); 5.08 (s, 1H, hydroxyl); 5.35 (dd, 1H, H₂··, $J_{H1''H2''}$=15.5, $J_{H2''H3''}$=6.1); 5.46 (dd, 1H, H₁··, $J_{H1''H2''}$= 15.5, $J_{H1''H3''}$=6.1); 7.14 (m, 3H, H₉··, H₁₁··, H₁₃··); 7.24 (t, 2H, 3J=7.5, H₁₀··, H₁₂··)

compound of Example 69: (the more polar isomer)

(1S*,3S*)-1-hydroxy-3-[(3R*S*,E)-3-hydroxy-7-phenyl-1-hepten-1-yl]cyclohexane-1-(N,N-dimethylacetamide) 1.0 (m, 2H, H₂·); 1.14 to 1.83 (m, 12H, H₄·, to H₆·; H₄·· to H₆··); 2.41 (s, 2H, H₂); 2.43 (m, 1H, H₃); 2.57 (t, 2H, H₇··); 2.94 (s, 3H, N-CH₃); 3.02 (s, 3H, N-CH₃); 3.98 (q, 1H, H₃··, $J_{H3''H4''}$=$J_{H3''H2''}$=6.4) 5.40 (dd, 1H, H₂··, $J_{H1''H2''}$=15.5, $J_{H2''H3''}$=6.1); 5.51 (dd, 1H, H₁··, $J_{H1''H2''}$=15.5 Hz, $J_{H1''H3''}$= 6.1 Hz); 5.70 (m, 1H, hydroxyl); 7.14 (m, 3H, H₉··, H₁₁··, H₁₃··); 7.24 (t, 2H, ³J=7.5, H₁₀··, H₁₂··)

| Percentage analysis C₂₃H₃₄NO₃ M: 373.261 | | | | | |
|---|---|---|---|---|---|
| Calc %: | C | 73.94 | H | 9.45 | N 3.75 |
| Measured: | | 74.02 | | 9.65 | 3.71 |

EXAMPLES 70 AND 71

EXAMPLE 70

(1R*,3S*)-1-HYDROXY-3-[(3S*R*,E)-3-HYDROXY-7-PHENYL-1-HEPTEN-1-YL]CYCLOHEXANE-1-(N,N-DIMETHYLACETAMIDE)

EXAMPLE 71

(1R*,3S*,E)-1-HYDROXY-3-[(3R*S*,E)-3-HYDROXY-7-PHENYL-1-HEPTEN-1-YL]CYCLOHEXANE-1-(N,N-DIMETHYLACETAMIDE)

The reaction is carried out as for the compound of Example 66, on 355 mg (0.728 mmol) of compound of Example 67. The 230 mg of oil obtained after chromatography are purified by HPLC (eluent: ethyl acetate). 214 mg (0.305 mmol) of pure compounds of Examples 70 and 71 are isolated. Overall yield=214 mg (0.574 mmol)=79%

IR (film, cm⁻¹): 3410 (vOH); 1720 (vC=O); 1180 (vC—O—C); 960 (vHC=CH trans)

¹H NMR (CDCl₃, 360 MHz) δ:
compound of Examples 70 and 71
(1R*,3S*)-1-hydroxy-3-[(E)-3-hydroxy-7-phenyl-1-hepten-1-yl]cyclohexane-1-(N,N-dimethylacetamide) 0.97 (m, 2H, H₂·); 1.13 to 1.9 (m, 12H, H₄·, to H₆·; H₄··to H₆··); 2 (m, 1H, H₃·); 2.52 (s, 2H, H₂); 2.53 (t, 2H, H₇··, J=7.4); 2.94 (s, 3H, N-CH₃); 3.02 (s, 3H, CH₃); 3.95 (q, 1H, H₃···, $J_{H3''H4''}=J_{H3''H2''}=6.4$); 5.37 (dd, 1H, H₂···, $J_{H1''H2''}=15.5$, $J_{H2''H3''}=6.1$); 5.5 (dd, 1H, H₁···, $J_{H1''H2''}=15.5$, $J_{H1''H3''}=6.1$); 5.7 (m, 1H, hydroxyl); 7.14 (m, 3H, H₉··, H₁₁··, H₁₃··); 7.24 (t, 2H, ³ J=7.5, H₁₀··, H₁₂··)

| Percentage analysis C₂₃H₃₄NO₃ M: 373.261 | | | | | |
|---|---|---|---|---|---|
| Calc %: | C | 73.94 | H | 9.45 | N 3.75 |
| Measured: | | 74.02 | | 9.48 | 3.70 |

EXAMPLES 72 AND 73

Employing the procedure described in the examples 66 and 67, but replacing N,N-dimethylacetamide by the N-methyl N-phenylacetamide, the followings are obtained:

EXAMPLE 72

(1S*,3S*)-1-HYDROXY-3-[(E)-3-HYDROXY-7-PHENYL-1-HEPTEN-1-YL]CYCLOHEXANE-1-(N-METHYL-N-PHENYLACETAMIDE)

EXAMPLE 73

(1R*,3S*)-1-HYDROXY-3-[(E)-3-HYDROXY-7-PHENYL-1-HEPTEN-1-YL]CYCLOHEXANE-1-(N-METHYL-N-PHENYLACETAMIDE)

EXAMPLES 74 AND 75

Employing the procedure described in the examples 66 and 67, but replacing N,N-dimethylacetamide by the N,N-dipropylacetamide, the followings are obtained:

EXAMPLE 74

(1S*,3S*)-1-HYDROXY-3-[(E)-3-HYDROXY-7-PHENYL-1-HEPTEN-1-YL]CYCLOHEXANE-1-(N,N-DIPROPYLACETAMIDE)

EXAMPLE 75

(1R*,3S*)-1-HYDROXY-3-[(E)-3-HYDROXY-7-PHENYL-1-HEPTEN-1-YL]CYCLOHEXANE-1-(N,N-DIPROPYLACETAMIDE)

EXAMPLE 76

ETHYL (1S*,3S*)-1-HYDROXY-3-[(E)-3-OXO-7-PHENYL-1-HEPTEN-1-YL]-1-CYCLOHEXANEACETATE

According to D. TAUB, R. D. HOFFSOMMER, C. H. KUO, H. L. SLATES, Z. S. ZELANSKI, N. L. WENDLER, Tetrahedron, 1973, 1447.

0.120 g (0.320 mmol) of compound of Example 5 dissolved in 10 cm³ of dichloromethane is introduced into a 25-cm³ round-bottomed flask. 2 g of activated manganese are added, and the medium is stirred for 16 h at room temperature. It is filtered through Celite, the filter is rinsed with dichloromethane and the filtrate is concentrated in a rotary evaporator. 0.105 g of an oil is obtained, which product is chromatographed by HPLC (eluent: cyclohexane/ethyl acetate, 90:10); 0.097 g (0.260 mmol) of pure ketone is thereby collected.

Yield (oxidation+HPLC chromatography): 81%

IR (film, cm⁻¹):

¹H NMR (CDCl₃, 100 MHz) δ: 3410 (vOH); 1720 (vC=O); 1185 (vC—O—C); 960 (vHC=CH trans) ¹H NMR (CDCl₃, 100 MHz) 0.75 to 2.15 (m, 15H, H₂·, ester methyl, H₄·to H₆·H₅··, H₆·); 2.2 to 2.80 (m, 7H, H₂, H₃·H₄··, H₇··); 3.57 (s, 1H, OH); 4.15 (q, 2H, ester methylene, J=7.2); 5.94 (d, 1H, H₂·, $J_{H1''}=16$); 6.72 (dd, 1H, H₁··, $J_{H1''H2''}=16$, $J_{H1''H3''}=6.1$); 7.18 (m, 5H, aromatic H)

| Percentage analysis: C₂₃H₃₂O₄ M = 374.52 | | | | |
|---|---|---|---|---|
| Calc %: | C | 74.15 | H | 8.66 |
| Measured: | | 74.05 | | 8.74 |

The compound thereby obtained may also be reduced using a reduction of the type described in Stage E' of Preparation 1.

The compound of the example 7 may also be oxyded by using this process. PHARMACOLOGICAL EXAMPLES

EXAMPLE A

STUDY OF BINDING OF THE COMPOUNDS OF THE INVENTION TO LTB₄ (Leukotriene B₄) RECEPTORS Study of the affinity of the compounds of the invention for LTB₄ receptors is carried out on human polymorphonuclear leukocytes (PMN), which are known for the presence of LTB₄ receptors on their membranes (J. Immunol. 1982, vol. 129, p 1600).

PROTOCOL

1) Obtaining human PMN

Human PMN are isolated from heparinized venous blood of healthy donors by sedimentation on dextran T₅₀₀. The supernatant is centrifuged on Ficoll Paque®, and the residual erythrocytes are removed by hypotonic lysis. The PMN are washed with Hank's isotonic saline solution (HBSS) free from $Ca^{2+}$ and $Mg^{2+}$.

Cellular purity is verified by the trypan blue exclusion technique.

Study of binding to $LTB_4$ receptors

Binding to PMN is carried out in HBSS free from $Ca^{2+}$ and $Mg^{2+}$ containing 5 mM HEPES buffer.

The PMN ($10^6$ cells) are incubated for 20 min at 4° C. with 1 nM [$^3$H]$LTB_4$ in the presence or absence of non-radioactive $LTB_4$ or of the compounds of the invention at various concentrations.

RESULTS

Incubation of human PMN with [$^3$H]$LTB_4$ (1 nM) in the presence of increasing doses of unlabeled $LTB_4$ permits a dose-dependent displacement of the [$^3$H]$LTB_4$ from its specific binding sites.

The compounds of the invention prove to be potent ligands for $LTB_4$ receptors, since they permit a 50% inhibition of the binding of [$^3$H]$LTB_4$ ($IC_{50}$) at concentrations of the order of $10^{-6}$ to $10^{-7}$M.

As an example, the compound of Example 7 permits a 50% inhibition ($IC_{50}$) of the binding of [$^3$H]$LTB_4$ at a concentration of $2 \times 10^{-7}$M. The compounds of Examples 69 and 71 also enable an $IC_{50}$ of $5 \times 10^{-7}$M and $2 \times 10^{-6}$M, respectively, to be obtained.

EXAMPLE B

STUDY OF THE ACTIVITY OF THE COMPOUNDS OF THE INVENTION WITH RESPECT TO THE CHEMOTAXIS OF HUMAN PMN IN VITRO $LTB_4$ causes an activation of the spontaneous migration of human PMN. Measurement of the inhibition of this migration hence enables the antagonist activity of the compounds of the invention with respect to $LTB_4$ to be tested.

PROTOCOL

PMN incubated in HBSS without $Ca^{2+}$ or $Mg^{2+}$ are labeled with $^{51}$chromium (1 μL Ci/$10^6$ cells) for 1 hour at 37° C. and then washed twice with HBSS.

The PMN are then resuspended at a concentration of $10^7$ cells/$cm^3$ in Hank's buffer with the addition of 1% bovine albumin. $LTB_4$ and the compounds of the invention dissolved in Hank buffer are introduced into the lower part of BOYDEN-KELLER chambers, two cellulose nitrate filters (Millipore, 3 μm) are placed on each well and the upper part of the chambers is filled with the cell suspension (Methods Enzymol 1988, vol. 162, pp 59–64).

The chambers are incubated for 150 min at 37° C. under an atmosphere of 95% humidified air and 5% $CO_2$.

The radioactivity of the lower filter is measured with a scintillation spectrometer (Beckman LS 3801).

RESULTS $LTB_4$ (0.1 to 100 nM) causes an activation of the spontaneous migration of human PMN through the filters of the BOYDEN-KELLER chambers.

The compounds of the invention prove to be potent $LTB_4$ antagonists, since they inhibit $LTB_4$-induced cell chemotaxis in a dose-dependent manner.

As an example, the compound of Example 7, up to a concentration of 50 μM, permits total inhibition of the action of $LTB_4$ on cell migration.

EXAMPLE C

STUDY OF THE ACTIVITY OF THE COMPOUNDS OF THE INVENTION WITH RESPECT TO THE CONTRACTION OF PARENCHYMATOUS LUNG STRIPS $LTB_4$ has a contracting effect on isolated parenchymatous strips of guinea pig lung. The antagonist activity of the compounds of the invention with respect to this $LTB_4$-induced contraction is tested.

PROTOCOL

Parenchymatous strips of DUNKIN HARTLEY guinea pig lung are cut and placed in baths containing Tyrode's solution oxygenated with a stream of gas (95% $O_2$/5% $CO_2$). The strips are connected to a polygraph (GOULD Statham) with an isometric tension of 400 mg. After 1 h of equilibrium, 1 μM mepyramine and 10 μM atroprine are added to the Tyrode's solution, and the compounds of the invention are tested for their antagonist activities. The contractile responses are recorded over 5 min. The antagonist activities of the compounds of the invention are tested by adding these compounds to the bath 2 min before stimulation of contraction with 30 nM $LTB_4$.

RESULTS

The compounds of the invention prove to be noteworthy $LTB_4$ antagonists, since they antagonize $LTB_4$-induced pulmonary parenchymatous contraction.

The concentrations of the compounds of the invention which produce a 50% inhibition of the contraction ($IC_{50}$) prove to be amazingly low. As an example, the $IC_{50}$ of the compound of Example 7 is 40 nM.

EXAMPLE D

STUDY OF THE ACTIVITY OF THE COMPOUNDS OF THE INVENTION WITH RESPECT TO A TOPICAL INFLAMMATORY MODEL (psoriasis)

Psoriasis is a chronic skin disorder having an inflammatory mechanism. It has been shown that T cells play a major part in the pathological process. In particular, the dermal infiltration of neutrophils into the psoriatic lesions has been linked to chemotactic factors such as $LTB_4$.

The present test enables the anti-inflammatory activity of the compounds of the invention with respect to such dermal lesions to be tested.

PROTOCOL (Current Test Protocols-Pharmacology Service-Panlabs-June 92).

Arachidonic acid (2 mg in 20 μl of an acetone/pyridine/water (7:2:1) mixture) is applied topically to the anterior and posterior surfaces of the right ear of a mouse 30 min after a similar application of the test compound or of the vehicle (20 μl). The swelling of the ear is measured by a Dyer type gauge after 60 min as an index of the inflammation.

The percentage inhibition is calculated according to the formula: Ic-It/Ic×100, in which Ic and It represent the increase in thickness (in mm) of the ear in the control mouse and in the treated mouse, respectively.

RESULTS

It is apparent that the compounds of the invention are potent topical anti-inflammatories.

For example, the compound of Example 7 permits a 30% decrease in the volume of the ear at a dose of 20 mg/ear.

EXAMPLE E

STUDY OF ACUTE TOXICITY

The acute toxicity was assessed after oral administration to groups of 8 mice (26±2 grams). The animals were observed at regular intervals during the first day and daily during the two weeks following the treatment. The $LD_{50}$, leading to the death of 50% of the animals, was evaluated.

The $LD_{50}$ of the test products is greater than 1000 mg.kg$^{-1}$ for the compounds studied, indicating the low toxicity of the compounds of the invention.

We claim:

1. A compound selected from those of formula (I):

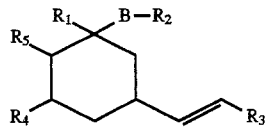

in which:

B represents an alkylene chain of 1 to 4 carbon atoms, inclusive unsubstituted or substituted with 1 or 2 alkyl, $R_1$ represents hydrogen or a radical chosen from hydroxyl and alkoxy, $R_2$ represents a radical chosen from: —$CH_2$—OH and

in which $R_6$ represents a group chosen from hydroxyl, alkoxy and

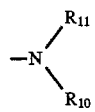

in which $R_{10}$ and $R_{11}$ each represent, independently of one another, hydrogen, alkyl, or aryl, arylalkyl, aryl or arylalkyl being unsubstituted or substituted on the aryl with one or more radicals chosen from halogen, alkyl, alkoxy, and trifluoromethyl, $R_3$ represents a group of formula:

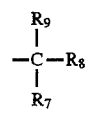

in which:

$R_7$ represents a radical chosen from hydroxyl, alkoxy and —O—$R_A$ in which $R_A$ represents acyl or at group protecting the hydroxyl function, $R_9$ represents hydrogen or alternatively $R_7$ and $R_9$ form an oxo group, and $R_8$ represents linear or branched alkyl having 1 to 12 carbon atoms inclusive, unsubstituted or substituted with one or more radicals chosen from:

unsubstituted aryl, aryl substituted with one or more radicals chosen from halogen, hydroxyl, alkyl, alkoxy and trifluoromethyl, unsubstituted cycloalkyl, $R_4$ and $R_5$ each represent, hydrogen, or alternatively $R_4$ and $R_5$ form, together with the cyclohexane which carries them, 1,2,3,4-tetrahydronaphthalene or perhydronaphthalene, on the understanding that, in the description of the formula (I) and except where otherwise specified:

the terms "alkyl", "alkoxy" and "acyl" denote linear or branched groups containing 1 to 6 carbon atoms, the term "aryl" denotes phenyl or naphthyl, the term "cycloalkyl" denotes a group having 3 to 7 carbon atoms inclusive, its enantiomers and diastereoisomers, its Z and E isomers, and its addition salts with a pharmaceutically-acceptable acid or base.

2. A compound selected from those claimed in claim 1 in which $R_8$ represents an unsubstituted linear or branched alkyl group having 1 to 12 carbon atoms inclusive, its enantiomers and diastereoisomers, its Z and E isomers, and its addition salts with a pharmaceutically-acceptable acid or base.

3. A compound selected from those claimed in claim 1 in which $R_8$ represents a linear or branched alkyl group having 1 to 12 carbon atoms inclusive substituted with unsubstituted or substituted phenyl, its enantiomers and diastereoisomers, its Z and E isomers, and its addition salts with a pharmaceutically-acceptable acid or base.

4. A compound selected from those claimed in claim 1 in which $R_7$ represents hydroxyl, its enantiomers and diastereo-isomers, its Z and E isomers, and its addition salts with a pharmaceutically-acceptable acid or base.

5. A compound as claimed in claim 1 which is ethyl 1-hydroxy-3-[(E)-3-tert-butyldimethylsilyloxy-7-phenyl1-hepten-1-yl]-1-cyclohexaneacetate.

6. The compound as claimed in claim 1 which is ethyl (1S*,3S*)-1-hydroxy-3-[(E)-3-tert-butyldimethylsilyloxy-7-phenyl-1-hepten-1-yl]-1-cyclohexaneacetate.

7. A compound as claimed in claim 1 which is ethyl (1S*,3S*)-1-hydroxy-3-[(3R*S*,E)-3-hydroxy-7-phenyl-1-hepten-1-yl]-1-cyclohexaneacetate.

8. A pharmaceutical composition containing as active principle a compound as claimed in claim 1, in combination with one or more pharmaceutically-acceptable excipients or vehicles.

9. A method of treating a mammal afflicted with psoriasis comprising the step of administering to the said mammal an effective amount of a compound as claimed in claim 1 for alleviation of said disorder.

* * * * *

UNITED STATES PATENT AND TRADEMARK OFFICE
CERTIFICATE OF CORRECTION

PATENT NO. : 5,639,902
DATED : June 17, 1997
INVENTOR(S) : J.P. Girard, P. Hullot, C. Bonne, J.C. Rossi, R. Escale, A. Muller Page 1 of 4

It is certified that error appears in the above-indentified patent and that said Letters Patent is hereby corrected as shown below:

Column 1, line 9: "monocles" should read -- monocytes --.

Column 7, line 20: "pads" should read -- parts --.

Column 8, line 9: "I h" should read -- 1 h --.

Column 8, line 63: "cm ):" should read -- $cm^{-1}$): --.

Column 8, line 63: "(vC-" should read -- (vC-O --.

Column 8, line 65: "$^1$H NMR CC14) δ:" should read -- $^1$H NMR (CC14) δ: --.

Column 9, line 52 (approx): "$^1$H NMR CC14) δ:" should read -- $^1$H NMR (CC14) δ: --.

Column 11, line 37: "$^1$H NMR $CCl_4$) δ:" should read -- $^1$H NMR ($CCl_4$) δ: --.

Column 11, line 39: "6.72 (dd, 1H, $H_{1'}$, $J_{H2}$= 16Hz," should read -- 6.72 (dd, 1H, $H_{1'}$, $J_{H1', H2'}$= 16Hz, --.

Column 12, line 12: "(HC=CH trans)" should read -- (vHC=CH trans) --.

UNITED STATES PATENT AND TRADEMARK OFFICE
CERTIFICATE OF CORRECTION

PATENT NO. : 5,639,902
DATED : June 17, 1997
INVENTOR(S) : J.P. Girard, P. Hullot, C. Bonne, J.C. Rossi, R. Escale, A. Muller It is certified that error appears in the above-indentified patent and that said Letters Patent is hereby corrected as shown below:

Column 12, line 13: "$^1$H NMR (CC14) δ:" should read -- $^1$H NMR (CC1$_4$) δ: --.

Column 13, line 56: "(vSi-OH$_3$);" should read -- (vSi-CH$_3$); --.

Column 13, line 57: "(vSi-OH$_3$)" should read -- (vSi-CH$_3$) --.

Column 14, line 16: "(vHC=OH trans);" should read -- (vHC=CH trans); --.

Column 17, line 55: Delete "[" at the end of the line.

Column 17, line 56: Insert -- [ -- at the beginning of the line.

Column 21, line 2: "960(vHC=OH trans);" should read -- 960(vHC=CH trans); --.

Column 21, line 10: "$J_{H3''H4''}=H_{H3''H2''}=6.4$ Hz);" should read -- $J_{H3''H4''}=J_{H3''H2''}=6.4$ Hz); --.

Column 21, line 49: "1.05(m,2H,H$_2$0;" should read -- 1.05(m,2H,H$_2$.); --.

Column 27, line 28: "SIL SiO$_2$ 10p. column, L 250, 22" should read -- SIL SiO$_2$ 10 μ column, L 250, Ø 22 --

UNITED STATES PATENT AND TRADEMARK OFFICE
CERTIFICATE OF CORRECTION

PATENT NO. : 5,639,902
DATED : June 17, 1997
INVENTOR(S) : J.P. Girard, P. Hullot, C. Bonne, J.C. Rossi, R. Escale, A. Muller Page 3 of 4

It is certified that error appears in the above-indentified patent and that said Letters Patent is hereby corrected as shown below:

Column 27, line 60: "5.32 (dd, 1H, $J_{H2'',H1''}$=6.1," should read -- 5.32 (dd, 1H, $J_{H2'',H3''}$=6.1, --.

Column 28, line 57: "3J=7.5, $H_{10'',}H_{12''}$)" should read -- $^3J$=7.5, $H_{10''},H_{12''}$) --.

Column 29, line 17: "(1R*,3S*,E)-" at the beginning of the line, should read -- (1R*,3S*)- --.

Column 30, line 32: Delete "$^1$H NMR (CDCl$_3$, 100 MHz) δ:".

Column 30, line 34: Insert -- δ: -- after "100 MHz)".

Column 30, line 35: "methyl, $H_{4'}$ to $H_{6'},H_{5''},H_{6''}$);" should read -- methyl, $H_{4'}$ to $H_{6''},H_{5''},H_{6''}$); --.

Column 30, line 37: "5.94 (d,1H,$H_{2''},J_{H1''}$ = 16);" should read -- 5.94 (d,1H,$H_{2''},J_{H1'',H2''}$=16); --.

Column 30, line 50: "PHARMACOLOGICAL EXAMPLES" should begin a new paragraph.

Column 31, line 5: Insert -- 2) -- at the beginning of the line.

Column 31, line 38: "(1 L Ci/10$^6$ cells)" should read (1 Ci/10$^6$ cells)--.

UNITED STATES PATENT AND TRADEMARK OFFICE
CERTIFICATE OF CORRECTION

PATENT NO. : 5,639,902
DATED : June 17, 1997
INVENTOR(S) : J.P. Girard, P. Hullot, C. Bonne, J.C. Rossi, R. Escale, A. Muller It is certified that error appears in the above-indentified patent and that said Letters Patent is hereby corrected as shown below:

Column 33, line 35: This line should read -- one another, hydrogen, alkyl, aryl, or arylalkyl, aryl or --.

Column 34, line 6: Delete the "," (comma) after "represent".

Column 34, line 13: Insert -- inclusive, -- after "1 to 6 carbon atoms"

Column 34, line 38: Last word in sentence "phenyll-" should read -- phenyl-1- --.

Signed and Sealed this

Twenty-first Day of October 1997

Attest:

BRUCE LEHMAN

Attesting Officer     Commissioner of Patents and Trademarks